United States Patent [19]
Schaper et al.

[11] Patent Number: 5,852,023
[45] Date of Patent: *Dec. 22, 1998

[54] CYCLOHEXYLAMINO AND CYCLOALKOXY NITROGEN HETEROCYCLES, PROCESSES FOR THEIR PREPARATION, AND THEIR USE AS PESTICIDES AND FUNGICIDES

[75] Inventors: Wolfgang Schaper, Schaper; Gerhard Krautstrunk, Frankfurt; Werner Knauf, Eppstein; Ulrich Sanft, Hofheim; Manfred Kern, Lörzweiler; Sergej Pasenok, Liederbach; Dieter Bernd Reuschling, Butzbach; Adolf Heinz Linkies, Frankfurt; Werner Bonin, Kelkheim, all of Germany

[73] Assignee: Hoechst Schering AgrEvo GmbH, Berlin, Germany

[ * ] Notice: The term of this patent shall not extend beyond the expiration date of Pat. Nos. 5,595,992, and 5,691,321.

[21] Appl. No.: 622,741

[22] Filed: Mar. 27, 1996

[30] Foreign Application Priority Data

Mar. 29, 1995 [DE] Germany ................. 195 11 562.7

[51] Int. Cl.$^6$ ............ A61K 31/505; C07D 239/02; C07D 415/00
[52] U.S. Cl. ............ 514/256; 514/63; 514/269; 544/229; 544/298; 544/319; 544/322; 544/326; 544/327; 544/328; 544/329; 544/333; 544/334; 544/335
[58] Field of Search ............ 544/229, 298, 544/319, 322, 326, 327, 328, 329, 333, 334, 335; 514/63, 256, 269

[56] References Cited

U.S. PATENT DOCUMENTS 5,571,815  11/1996  Schaper et al. ............ 514/269
5,595,992  1/1997   Preuss et al. ............ 514/254
5,691,321  11/1997  Schaper et al. ............ 514/63

FOREIGN PATENT DOCUMENTS

| A 44 17 163 | 11/1995 | Germany . |
| WO 92/08704 | 5/1992  | WIPO . |
| WO 93/22291 | 2/1993  | WIPO . |
| WO 92 19050 | 9/1993  | WIPO . |
| WO 95/07278 | 3/1995  | WIPO . |
| WO 96/06086 | 2/1996  | WIPO . |

OTHER PUBLICATIONS

Pacquet et al., Synthesis of New Carbocyclic Analogues of Oxetanocin A and Oxetanocin G, Heterocycles, vol. 34, No. 4, pp. 739–745, 1992.

*Primary Examiner*—Richard L. Raymond
*Assistant Examiner*—Brenda Coleman
*Attorney, Agent, or Firm*—Frommer Lawrence & Haug LLP

[57] ABSTRACT

Cyclohexylamino and cycloalkoxy nitrogen heterocycles, processes for their preparation, and their use as pesticides and fungicides.

The invention relates to compounds of the formula

Ar—X-E-Q in which Ar is substituted or unsubstituted 4-pyridyl or 4-pyrimidinyl; X is NH, O, S, SO or $SO_2$; E is a bond or alkanediyl; and Q is a substituted cycloalkyl or 4-piperidyl.

The invention also relates to processes and intermediates for their preparation, to compositions comprising them and to their use as pesticides and fungicide.

19 Claims, No Drawings

CYCLOHEXYLAMINO AND CYCLOALKOXY NITROGEN HETEROCYCLES, PROCESSES FOR THEIR PREPARATION, AND THEIR USE AS PESTICIDES AND FUNGICIDES

It is already known that certain 4-cycloalkylamino and 4-cycloalkoxy nitrogen heterocycles possess an insecticidal, acaricidal, ixodicidal and fungicidal action (WO 93 00536).

Novel 4-amino- and 4-alkoxy-substituted nitrogen heterocycles have now been found of the formula I

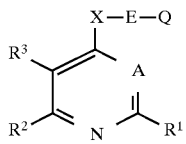 (I)

in which the radicals and groups are as defined below, which, while showing good tolerance by plants and favorable toxicity toward warm-blooded animals, are highly suitable for controlling animal pests, such as insects, arachnids, nematodes, helminths and molluscs, for controlling endoparasites and ectoparasites in the veterinary field, and for controlling harmful fungi.

The invention therefore relates to compounds of the formula I in which $R^1$ is hydrogen, halogen, $(C_1-C_4)$-alkyl or $(C_3-C_5)$-cycloalkyl;

$R^2$ and $R^3$ are identical or different and are each hydrogen, $(C_1-C_4)$-alkyl, $(C_1-C_4)$-haloalkyl, $(C_2-C_4)$-alkenyl, $(C_2-C_4)$-haloalkenyl, $(C_2-C_4)$-alkynyl, $(C_2-C_4)$-haloalkynyl, $(C_1-C_8)$-trialkylsilylalkynyl, preferably dimethyl-$(C_1-C_8)$-alkylsilylalkynyl, phenyl-$(C_1-C_8)$-dialkylsilylalkynyl, preferably phenyldimethylsilylalkynyl, aryl-$(C_1-C_2)$-alkyl-$(C_1-C_8)$-dialkylsilylalkynyl, preferably benzyldimethylsilylalkynyl, $(C_3-C_8)$-cycloalkyl-$(C_1-C_8)$-dialkylsilylalkynyl, preferably $(C_3-C_8)$-cycloalkyldimethylsilylalkynyl, (1-methylsila-$(C_3-C_8)$-cycloalk-1-yl)alkynyl, preferably (1-methylsilacyclopent-1-yl)alkynyl or (1-methylsilacyclohex-1-yl)alkynyl, triphenylsilylalkynyl, $(C_1-C_4)$-alkoxy, $(C_1-C_4)$-haloalkoxy, $(C_1-C_4)$-alkoxy-$(C_1-C_4)$-alkyl, $(C_1-C_4)$-haloalkoxy-$(C_1-C_4)$-alkyl, $(C_1-C_4)$-alkoxy-$(C_1-C_4)$-haloalkyl, $(C_1-C_4)$haloalkoxy-$(C_1-C_4)$-haloalkyl, halogen, hydroxyl, $(C_1-C_4)$-hydroxyalkyl, $(C_1-C_4)$-alkanoyl, $(C_1-C_4)$-alkanoyl-$(C_1-C_4)$-alkyl, $(C_1-C_4)$-haloalkanoyl, $(C_3-C_5)$-cycloalkyl, $(C_3-C_5)$-halocycloalkyl, cyano, $(C_1-C_4)$-cyanoalkyl, nitro, $(C_1-C_4)$-nitroalkyl, thiocyano, $(C_1-C_4)$-thiocyanoalkyl, $(C_1-C_4)$-alkoxycarbonyl, $(C_1-C_4)$-alkoxycarbonyl-$(C_1-C_4)$-alkyl, $(C_1-C_4)$-haloalkoxycarbonyl, $(C_1-C_4)$-alkanoyloxy-$(C_1-C_4)$-alkyl, $(C_1-C_4)$-alkylthio, $(C_1-C_4)$-alkylthio-$(C_1-C_4)$-alkyl, $(C_1-C_4)$-haloalkylthio, $(C_1-C_4)$-alkylsulfinyl, $(C_1-C_4)$-haloalkyl-sulfinyl, $(C_1-C_4)$-alkylsulfonyl or $(C_1-C_4)$-haloalkylsulfonyl; where, if $R^2$ is hydrogen, $(C_1-C_4)$-alkyl, halogen, $(C_1-C_4)$-haloalkyl, $(C_1-C_4)$-alkoxy, $(C_1-C_4)$-haloalkoxy, $(C_1-C_4)$-alkoxy-$(C_1-C_4)$-alkyl, $(C_1-C_4)$-alkylthio or $(C_1-C_4)$-alkylthio-$(C_1-C_4)$-alkyl;

$R^3$ is not simultaneously hydrogen, $(C_1-C_4)$-alkyl, $(C_1-C_4)$-alkoxy, $(C_1-C_4)$-haloalkoxy, halogen or $(C_1-C_4)$-alkylthio;

A is nitrogen and, if $R^2$ or $R^3$ is $(C_2-C_4)$-alkynyl, $(C_1-C_8)$-trialkylsilylalkynyl, preferably dimethyl-$(C_1-C_8)$-alkylsilylalkynyl, phenyl-$(C_1-C_8)$-dialkylsilylalkynyl, preferably phenyldimethylsilylalkynyl, aryl-$(C_1-C_2)$-alkyl-$(C_1-C_8)$-dialkylsilylalkynyl, preferably benzyldimethylsilylalkynyl, $(C_3-C_8)$-cycloalkyl-$(C_1-C_8)$-dialkylsilylalkynyl, preferably $(C_3-C_8)$-cycloalkyldimethylsilylalkynyl, (1-methylsila-$(C_3-C_8)$-cycloalk-1-yl)alkynyl, preferably (1-methylsilacyclopent-1-yl)alkynyl or (1-methylsilacyclohex-1-yl)alkynyl, triphenylsilylalkynyl, $(C_2-C_4)$-haloalkynyl, $(C_2-C_4)$-hydroxyalkyl, $(C_1-C_4)$-alkanoyl, $(C_1-C_4)$-haloalkanoyl, $(C_1-C_4)$-alkanoyl-$(C_1-C_4)$-alkyl, $(C_3-C_5)$-cycloalkyl, $(C_3-C_5)$-halocycloalkyl, $(C_1-C_4)$-cyanoalkyl, thiocyano, $(C_1-C_4)$-thiocyanoalkyl, hydroxyl, $(C_1-C_4)$-alkylthio-$(C_1-C_4)$-alkyl, nitro, $(C_1-C_4)$-nitroalkyl, $(C_1-C_4)$-alkoxycarbonyl-$(C_1-C_4)$-alkyl, $(C_1-C_4)$-haloalkylthio, $(C_1-C_4)$-haloalkylsulfinyl, $(C_1-C_4)$-haloalkylsulfonyl, $(C_1-C_4)$-alkoxy-$(C_1-C_4)$-haloalkoxy or $(C_1-C_4)$-haloalkoxy-$(C_1-C_4)$-haloalkyl, is alternatively CH;

X is NH, oxygen or $S(O)_q$ where q is 0, 1 or 2;

E is a direct bond or a straight-chain or branched $(C_1-C_4)$-alkanediyl group, preferably a direct bond;

Q is as defined for $Q^1$, and $Q^1$ is a cycloalkyl group of the formula II or II'

 (II)

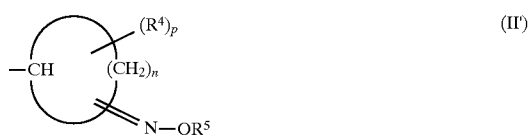 (II')

in which n is an integer from 2 to 7;

$(R^4)_p$ and $UR^5$ are substituents of the isocyclic ring formed with the participation of $(CH_2)_n$;

p is 1 or 2;

$R^4$ is hydrogen, halogen, $(C_1-C_4)$-alkyl, $(C_1-C_4)$-haloalkyl, $(C_1-C_4)$-alkoxy or $(C_1-C_4)$-alkylthio;

U is a direct bond, oxygen or a group $S(O)_m$ where m=0, 1 or 2;

$R^5$ is alkyl, alkenyl, alkynyl, aryl or heterocyclyl, and, if $Q^1$ is a radical of the formula II and U is a direct bond, is furthermore hydroxyl, cyano, thiocyano, nitro or halogen, it being possible for the aryl or heterocyclyl radicals mentioned to be unsubstituted or to be substituted by up to three—and in the case of fluorine up to the maximum number of—identical or different radicals and for one or more, preferably up to three, nonadjacent saturated carbon units in the alkyl, alkenyl or alkynyl radicals mentioned to be replaced by a carbonyl group or by heteroatom units, such as oxygen, $S(O)_x$ where x=0, 1 or 2, $NR^6$ or $SiR^7R^8$, in which $R^6$ is hydrogen, $(C_1-C_4)$-alkyl, $(C_1-C_4)$-alkoxy or $(C_1-C_4)$-alkanoyl and $R^7$ and $R^8$ are $(C_1-C_4)$-alkyl, preferably methyl;

and in which, furthermore, 3 to 12 atoms of these hydrocarbon radicals, which radicals are modified as above if desired, can form a ring and these hydrocarbon radicals, with or without the variations indicated, can if desired be substituted by one or more, preferably up to three—and in the case of fluorine up to the maximum number of—identical or different radicals from the series consisting of halogen, aryl, aryloxy, arylthio, cycloalkoxy, cycloalkylthio, heterocyclyl, heterocyclyloxy, heterocyclylthio, alkanoyl, cycloalkanoyl, haloalkanoyl, aroyl, arylalkanoyl, cycloalkylalkanoyl, heterocyclylalkanoyl, alkoxycarbonyl, haloalkoxycarbonyl, cycloalkoxycarbonyl, cycloalkylalkoxycarbonyl, arylalkoxycarbonyl, heterocyclylalkoxycarbonyl, aryloxycarbonyl, heterocyclyloxycarbonyl, alkanoyloxy, haloalkanoyloxy, cycloalkanoyloxy, cycloalkylalkanoyloxy, aroyloxy, arylalkanoyloxy, heterocyclylalkanoyloxy, alkylsulfonyloxy, arylsulfonyloxy, hydroxyl, cyano, thiocyano or nitro, it being possible for the cycloaliphatic, aromatic or heterocyclic ring systems among the substituents just mentioned to be unsubstituted or substituted by up to three—and in the case of fluorine up to the maximum number of—identical or different substituents, or Q is as defined for $Q^2$ and $Q^2$ is a radical of the formula III

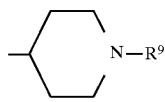
(III)

in which $R^9$ is aryl or heteroaryl and the aryl or heteroaryl group can be unsubstituted or substituted by up to three—and in the case of fluorine up to the maximum number of—identical or different substituents, and salts thereof, preferably acid addition salts;

especially those compounds for which $R^5$ is $(C_1-C_{20})$-alkyl, $(C_2-C_{20})$-alkenyl, $(C_2-C_{20})$-alkynyl, aryl, heterocyclyl, and, if $Q^1$ is a radical of the formula II and U is a direct bond, is furthermore hydroxyl, cyano, thiocyano, nitro or halogen, it being possible for the aryl or heterocyclyl radicals mentioned to be unsubstituted or to be substituted by up to three—and in the case of fluorine up to the maximum number of—identical or different radicals and for one or more, preferably up to three, nonadjacent saturated carbon units in the alkyl, alkenyl or alkynyl radicals mentioned to be replaced by a carbonyl group or by heteroatom units, such as oxygen, $S(O)_x$ where $x=0$, 1 or 2, $NR^6$ or $SiR^7R^8$, in which $R^6$ is hydrogen, $(C_1-C_4)$-alkyl, $(C_1-C_4)$-alkoxy or $(C_1-C_4)$-alkanoyl and $R^7$ and $R^8$ are $(C_1-C_4)$-alkyl, preferably methyl, and in which, furthermore, 3 to 12 atoms of these hydrocarbon radicals, which radicals are modified as above if desired, can form a ring and these hydrocarbon radicals, with or without the variations indicated, can if desired be substituted by one or more, preferably up to three—and in the case of halogen up to the maximum number of—identical or different radicals from the series consisting of halogen, aryl, aryloxy, arylthio, $(C_3-C_8)$-cycloalkoxy, $(C_3-C_8)$-cycloalkylthio, heterocyclyl, heterocyclyloxy, heterocyclylthio, $(C_1-C_{12})$-alkanoyl, $(C_3-C_8)$-cycloalkanoyl, $(C_1-C_{12})$-haloalkanoyl, aryl-$(C_1-C_4)$-alkanoyl, $(C_3-C_8)$-cycloalkyl-$(C_1-C_4)$-alkanoyl, heterocyclyl-$(C_1-C_4)$-alkanoyl, $(C_1-C_{12})$-alkoxycarbonyl, $(C_1-C_{12})$-haloalkoxycarbonyl, $(C_3-C_8)$-cycloalkoxycarbonyl, $(C_3-C_8)$-cycloalkyl-$(C_1-C_4)$-alkoxycarbonyl, aryl-$(C_1-C_4)$-alkoxycarbonyl, heterocyclyl-$(C_1-C_4)$-alkoxycarbonyl, aryloxycarbonyl, heterocyclyloxycarbonyl, $(C_1-C_{12})$-alkanoyloxy, $(C_2-C_{12})$-haloalkanoylalkoxy, $(C_3-C_8)$-cycloalkanoyloxy, $(C_3-C_8)$-cycloalkyl-$(C_1-C_4)$-alkanoyloxy, aroyloxy, aryl-$(C_1-C_4)$-alkanoyloxy, heterocyclyl-$(C_1-C_4)$-alkanoyloxy, $(C_1-C_{12})$-alkylsulfonyloxy, arylsulfonyloxy, hydroxyl, cyano, thiocyano or nitro, it being possible for the cycloaliphatic, aromatic or heterocyclic ring systems among the substituents just mentioned to be unsubstituted or substituted by up to three—and in the case of fluorine up to the maximum number of—identical or different substituents, and, in addition, if Q is as defined for $Q^1$, n is 5 and E is a direct bond, the groups -X-E and $UR^5$ are preferably in the cis configuration relative to one another and take up positions 1 and 4 on the cyclohexane ring.

Preferred compounds of the formula I are those in which $R^1$ is hydrogen or fluorine;

$R^2$ and $R^3$ are $(C_1-C_4)$-alkyl, $(C_2-C_4)$-alkenyl, $(C_2-C_4)$-alkynyl, trimethylsilylethynyl, methoxycarbonyl, $(C_1-C_4)$-haloalkyl, halogen, methoxymethyl or cyano;

A is CH or N;

X is NH or oxygen;

U is oxygen or a direct bond;

E is a direct bond;

n is 5; the radicals X and $UR^5$ or $NOR^5$ take up positions 1 and 4 on the cyclohexane ring and X and $UR^5$ are in the cis configuration relative to one another;

$R^4$ is hydrogen, $(C_1-C_4)$-alkyl, trifluoromethyl or $(C_1-C_4)$-alkoxy;

especially those compounds of the formula I in which $R^1$ is hydrogen;

$R^2$ and $R^3$ are methyl, ethyl, propyl, $(C_2-C_3)$-alkenyl, $(C_2-C_3)$-chloro- or fluoroalkenyl, $(C_2-C_3)$-alkynyl, trimethylsilylethynyl, $(C_1-C_3)$-chloro- or fluoroalkyl, methoxymethyl, halogen or cyano;

A is CH;

X is NH;

$R^4$ is hydrogen.

Compounds of the formula I which are most preferred are those for which $R^1$ is hydrogen;

$R^2$ is methyl, ethyl, vinyl, ethynyl, trimethylsilylethynyl, $(C_1-C_2)$-fluoroalkyl or methoxymethyl;

$R^3$ is vinyl, ethynyl, trimethylsilylethynyl, methyl, ethyl, $(C_1-C_2)$-fluoroalkyl, cyano or halogen;

A is nitrogen;

X is NH;

E is a direct bond;

$R^4$ is hydrogen;

n is 5;

Q is a radical of the formula II in which the substituents X and $UR^5$ take up positions 1 and 4 on the cyclohexane ring and are in each case in the cis configuration relative to one another, or Q is a radical of the formula II' in which the substituent X and the oxime ether group take up positions 1 and 4 on the cyclohexane ring;

$R^5$ is $(C_1-C_{12})$-alkyl, $(C_2-C_{12})$-alkenyl, $(C_2-C_{12})$-alkynyl, aryl or heterocyclyl, it being possible for the aryl or heterocyclyl radicals to be unsubstituted or to be substituted by up to three—and in the case of fluorine up to the maximum number of—identical or different radicals and for one, two or three, preferably one, carbon unit in the alkyl radicals mentioned to be replaced by heteroatom units, such as oxygen, sulfur or $SiR^7R^8$, and $R^7$ and $R^8$ are preferably methyl, and in which, furthermore, 3 to 12 atoms of these hydrocarbon radicals, which radicals can if desired be modified as above, can form a ring and these hydrocarbon radicals, with or without the variations indicated, can if desired be substituted by one or more, preferably up to three—and in the case of halogen up to the maximum number of—identical or different radicals from the series consisting of aryl, aryloxy, arylthio, heterocyclyl, heterocyclyloxy, heterocyclylthio and alkoxycarbonyl, it being possible for the aromatic or heterocyclic ring systems among the substituents just mentioned to be unsubstituted or to be substituted by up to three—and in the case of fluorine up to the maximum number of—identical or different substituents, especially those compounds for which Q is a radical of the formula II in which U is a direct bond;

$R^5$ is $(C_1-C_{12})$-alkyl or phenyl, and in the alkyl radicals one carbon unit can be replaced by $Si(CH_3)_2$ and/or oxygen and, furthermore, 3 to 6 atoms of this carbon chain, which chain can if desired be modified as above, can form a ring and the phenyl radical can be unsubstituted or substituted by up to three—and in the case of fluorine up to the maximum number of—identical or different radicals.

In the above formula, "halogen" ("halo") means a fluorine, chlorine, bromine or iodine atom, preferably a fluorine, chlorine or bromine atom;

"$(C_1-C_4)$-alkyl" means an unbranched or branched hydrocarbon radical having 1 to 4 carbon atoms, for example the methyl, ethyl, propyl, isopropyl, 1-butyl, 2-butyl, 2-methylpropyl or tert-butyl radical;

"$(C_1-C_{20})$-alkyl" means the abovementioned alkyl radicals, for example the pentyl, 2-methylbutyl or 1,1-dimethylpropyl radical, or the hexyl, heptyl, octyl, 1,1,3,3-tetramethylbutyl, nonyl, 1-decyl, 2-decyl, undecyl, dodecyl, pentadecyl or eicosyl radical;

"$(C_1-C_4)$-haloalkyl" means an alkyl group as specified for "$(C_1-C_4)$-alkyl", in which one or more hydrogen atoms have been replaced by the abovementioned halogen atoms, preferably chlorine or fluorine, for example the trifluoromethyl group, the 1-fluoroethyl group, the 2-fluoroethyl group, the 2,2,2-trifluoroethyl group, the chloromethyl, fluoromethyl or difluoromethyl group, or the 1,1,2,2-tetrafluoroethyl group;

"$(C_1-C_2)$-fluoroalkyl" means for example the 1-fluoroethyl, 2-fluoroethyl, 2,2-difluoroethyl, 1,1,-difluoroethyl or the 2,2,2-trifluoroethyl group;

"cycloalkyl" means preferably $(C_3-C_8)$-cycloalkyl;

"cycloalkoxy" means preferably $(C_3-C_8)$-cycloalkoxy;

"cycloalkylthio" means preferably $(C_3-C_8)$-cycloalkylthio;

"$(C_3-C_5)$-cycloalkyl" means the cyclopropyl, cyclobutyl or cyclopentyl group;

"$(C_3-C_8)$-cycloalkyl" means the radicals mentioned above under "$(C_3-C_5)$-cycloalkyl" plus the cyclohexyl, cycloheptyl and cyclooctyl radicals;

"$(C_3-C_5)$-halocycloalkyl" means one of the abovementioned $(C_3-C_5)$-cycloalkyl radicals in which one or more—and in the case of fluorine possibly all—of the hydrogen atoms have been replaced by halogen, preferably fluorine or chlorine, for example the 2,2-difluoro- or 2,2-dichlorocyclopropane group or the fluorocyclopentane radical;

"$(C_2-C_4)$-alkenyl" means for example the vinyl, allyl, 2-methyl-2-propenyl or 2-butenyl group;

"$(C_2-C_{20})$-alkenyl" means the abovementioned radicals plus for example the 2-pentenyl, 2-decenyl or 2-eicosenyl group;

"$(C_2-C_4)$-haloalkenyl" means a $(C_2-C_4)$-alkenyl group in which some—and in the case of fluorine possibly all—of the hydrogen atoms have been replaced by halogen, preferably fluorine or chlorine;

"$(C_2-C_4)$-alkynyl" means for example the ethynyl, propargyl, 1-butynyl, 2-butynyl or 3-butynyl group;

"$(C_2-C_{20})$-alkynyl" means the abovementioned radicals plus for example the 2-pentynyl or 2-decynyl group;

"$(C_2-C_4)$-haloalkynyl" means a $(C_2-C_4)$-alkynyl group in which some—and in the case of fluorine possibly all—of the hydrogen atoms have been replaced by halogen atoms, preferably fluorine or chlorine, or else means the iodoethynyl group;

"dimethyl-$(C_1-C_8)$-alkylsilylethynyl" means for example the trimethylsilylethynyl or the tert-butyldimethylsilylethynyl group;

"$(C_1-C_4)$-hydroxyalkyl" means for example the hydroxymethyl, 1-hydroxyethyl, 2-hydroxyethyl, 1-hydroxy-1-methylethyl or the 1-hydroxypropyl group;

"$(C_1-C_4)$-alkanoyl" means for example the formyl, acetyl, propionyl, 2-methylpropionyl or butyryl group;

"$(C_1-C_4)$-haloalkanoyl" means a $(C_1-C_4)$-alkanoyl group in which some—and in the case of fluorine possibly all—of the hydrogen atoms have been replaced by halogen atoms, preferably fluorine or chlorine;

"cyano-$(C_1-C_4)$-alkyl" means a cyanoalkyl group whose hydrocarbon radical is as defined under "$(C_1-C_4)$-alkyl";

"$(C_1-C_4)$-alkoxycarbonyl" means for example the methoxycarbonyl, ethoxycarbonyl, propoxycarbonyl, butoxycarbonyl or tert-butoxycarbonyl group;

"$(C_1-C_{12})$-alkoxycarbonyl" means the abovementioned radicals plus for example the hexyloxycarbonyl, 2-methylhexyloxycarbonyl, decyloxycarbonyl or dodecyloxycarbonyl group;

"$(C_1-C_4)$-haloalkoxycarbonyl" means a $(C_1-C_4)$-alkoxycarbonyl group in which one or more—and in the case of fluorine possibly all—of the hydrogen atoms have been replaced by halogen, preferably fluorine or chlorine;

"$(C_1-C_4)$-alkylthio" means an alkylthio group whose hydrocarbon radical is as defined for "$(C_1-C_4)$-alkyl";

"$(C_1-C_4)$-haloalkylthio" means a $(C_1-C_4)$-alkylthio group in which one or more—and in the case of fluorine possibly all—of the hydrogen atoms of the hydrocarbon moiety have been replaced by halogen, especially chlorine or fluorine;

"$(C_1-C_4)$-alkylsulfinyl" means for example the methyl-, ethyl-, propyl-, isopropyl-, butyl-, isobutyl-, sec-butyl- or tert-butylsulfinyl group;

"$(C_1-C_4)$-alkylsulfonyl" means for example the methyl-, ethyl-, propyl-, isopropyl-, butyl-, isobutyl-, sec-butyl- or tert-butylsulfonyl group;

"$(C_1-C_4)$-haloalkylsulfinyl" and "$(C_1-C_4)$-haloalkylsulfonyl" mean $(C_1-C_4)$-alkylsulfinyl and -sulfonyl radicals as defined above in which one or more—and in the case of fluorine possibly all—of the hydrogen atoms of the hydrocarbon moiety have been replaced by halogen, especially chlorine or fluorine;

"$(C_1-C_4)$-alkoxy" means an alkoxy group whose hydrocarbon radical is as defined under "$(C_1-C_4)$-alkyl";

"$(C_1-C_4)$-haloalkoxy" means a haloalkoxy group whose halogenated hydrocarbon radical is as defined under "$(C_1-C_4)$-haloalkyl";

"$(C_1-C_4)$-alkoxy-$(C_1-C_4)$-alkyl" means for example a 1-methoxyethyl group, a 2-methoxyethyl group, a 2-ethoxyethyl group, a methoxymethyl or ethoxymethyl group, a 3-methoxypropyl group or a 4-butoxybutyl group;

"$(C_1-C_4)$-haloalkoxy-$(C_1-C_4)$-alkyl", "$(C_1-C_4)$-alkoxy-$(C_1-C_4)$-haloalkyl" and "$(C_1-C_4)$-haloalkoxy-$(C_1-C_4)$-haloalkyl" mean $(C_1-C_4)$-alkoxy-$(C_1-C_4)$-alkyl radicals as defined above in which one or more—and in the case of fluorine possibly all—of the hydrogen atoms of the corresponding hydrocarbon moieties have been replaced by halogen, preferably chlorine or fluorine;

"$(C_1-C_4)$-alkylthio-$(C_1-C_4)$-alkyl" means for example methylthiomethyl, ethylthiomethyl, propylthiomethyl, 2-methylthioethyl, 2-ethylthioethyl or 3-methylthiopropyl;

"aryl" means an isocyclic aromatic radical having preferably 6 to 14, especially 6 to 12, carbon atoms, for example phenyl, naphthyl or biphenylyl, preferably phenyl;

"heterocyclyl" means a heteroaromatic or heteroaliphatic ring system, where "heteroaromatic ring system" means an aryl radical in which at least one CH group is replaced by N and/or at least two adjacent CH groups are replaced by S, NH or O, for example a radical of thiophene, furan, pyrrole, thiazole, oxazole, imidazole, isothiazole, isoxazole, pyrazole, 1,3,4-oxadiazole, 1,3,4-thiadiazole, 1,3,4-triazole, 1,2,4-oxadiazole, 1,2,4-thiadiazole, 1,2,4-triazole, 1,2,3-triazole, 1,2,3,4-tetrazole, benzo[b]thiophene, benzo[b]furan, indole, benzo[c]thiophene, benzo[c]furan, isoindole, benzoxazole, benzothiazole, benzimidazole, benzisoxazole, benzisothiazole, benzopyrazole, benzothiadiazole, benzotriazole, dibenzofuran, dibenzothiophene, carbazole, pyridine, pyrazine, pyrimidine, pyridazine, 1,3,5-triazine, 1,2,4-triazine, quinoline, isoquinoline, quinoxaline, quinazoline, cinnoline, 1,8-naphthyridine, 1,5-naphthyridine, 1,6-naphthyridine, 1,7-naphthyridine, phthalazine, pyridopyrimidine, purine, pteridine or 4H-quinolizine;

and "heteroaliphatic ring system" means a $(C_3–C_8)$-cycioalkyl radical in which at least one carbon unit has been replaced by O, S or a group $NR^{11}$, and $R^{11}$ is hydrogen, $(C_1–C_4)$-alkyl, $(C_1–C_4)$-alkoxy or aryl;

"arylthio" means for example the phenylthio group or the 1- or 2-naphthylthio group;

"aryloxy" means for example the phenoxy group or 1- or 2-naphthyloxy group;

"heterocyclyloxy" or "heterocyclylthio" means one of the abovementioned heterocyclic radicals which is linked via an oxygen or sulfur atom;

"$(C_3–C_8)$-cycloalkoxycarbonyl" means for example the cyclobutyloxycarbonyl, cyclopentyloxycarbonyl, cyclohexyloxycarbonyl or the cycloheptyloxycarbonyl group;

"$(C_3–C_8)$-cycloalkyl-$(C_1–C_4)$-alkoxycarbonyl" means for example the cyclopropylmethoxycarbonyl, cyclobutylmethoxycarbonyl, cyclopentyloxymethylcarbonyl, cyclohexyloxymethylcarbonyl, 1-(cyclohexyl)ethoxycarbonyl or the 2-(cyclohexyl)ethoxycarbonyl group;

"aryl-$(C_1–C_4)$-alkoxycarbonyl" means for example the benzyloxycarbonyl, 1-naphthylmethoxycarbonyl, 2-naphthylmethoxycarbonyl, 1-phenylethoxycarbonyl or the 2-phenylethoxycarbonyl group;

"aryloxycarbonyl" means for example the phenoxycarbonyl, naphthoxycarbonyl or the biphenyloxycarbonyl group;

"heterocyclyl-$(C_1–C_4)$-alkanoyl" means for example the thenoyl, furoyl, tetrahydrofurfurylcarbonyl, thienylacetyl or the pyridylacetyl group;

"heterocyclyl-$(C_1–C_4)$-alkoxycarbonyl" means for example the thienylmethoxycarbonyl, furylmethoxycarbonyl, pyridylmethoxycarbonyl or the thienylethoxycarbonyl group;

"$(C_1–C_{12})$-alkanoyloxy" means for example the formyloxy, acetoxy, propionyloxy, butyryloxy, pivaloyloxy, valeroyloxy or the decanoyloxy group;

"$(C_2–C_{12})$-haloalkanoyloxy" means a $(C_2–C_{12})$-alkanoyloxy group in which one or more—and in the case of fluorine possibly all—of the hydrogen atoms of the hydrocarbon moiety have been replaced by halogen, especially fluorine or chlorine;

"$(C_3–C_8)$-cycloalkanoyloxy" means for example the cyclopropanoyloxy, cyclobutanoyloxy, cyclopentanoyloxy, cyclohexanoyloxy or the cycloheptanoyloxy group;

"$(C_3–C_8)$-cycloalkyl-$(C_1–C_4)$-alkanoyloxy" means for example the cyclopropylcarbonyloxy, cyclopropylacetoxy, cyclobutylcarbonyloxy, cyclopentylcarbonyloxy, cyclohexylcarbonyloxy, cyclohexylacetoxy or the 4-cyclohexylbutyryloxy group;

"aroyloxy" means for example the benzoyloxy or the naphthoyloxy group;

"heterocyclyl-$(C_1–C_4)$-alkanoyloxy" means for example the thienylcarbonyloxy, thienylacetoxy, pyridylcarbonyloxy or the pyrimidinylcarbonyloxy group;

"aryl-$(C_1–C_4)$-alkanoyloxy" means for example the benzoyloxy, naphthoyloxy or the phenylacetoxy group;

"$(C_1–C_{20})$-alkylsulfonyloxy" means for example the methane-, ethane-, butane- or hexanesulfonyloxy group;

"arylsulfonyloxy" means for example the phenylsulfonyloxy or the toluenesulfonyloxy group.

Examples of the possible substituents for the various aliphatic, aromatic and heterocyclic ring systems include halogen, nitro, cyano, di-$(C_1–C_4)$-alkylamino, $(C_1–C_4)$-alkyl, $(C_1–C_4)$-trialkylsilyl, $(C_1–C_4)$-alkoxy, $(C_1–C_4)$-alkoxy-$(C_1–C_4)$-alkyl, $(C_1–C_2)$-alkoxy-$[CH_2CH_2]_{1,2}$-ethoxy, $(C_1–C_4)$-alkylthio, $(C_1–C_4)$-alkylsulfinyl, $(C_1–C_4)$-alkylsulfonyl, phenyl, benzyl, phenoxy, phenylthio, halophenoxy, $(C_1–C_4)$-alkylphenoxy, $(C_1–C_4)$-alkoxyphenoxy, $(C_1–C_4)$-alkylthiophenoxy, phenylthio, heterocyclyl, heterocyclylthio, heterocyclyloxy, haloheterocyclyloxy, alkylheterocyclyloxy or alkoxyheterocyclyloxy, where in the alkyl radicals and the radicals derived therefrom one or more—and in the case of fluorine up to the maximum number of—hydrogen atoms can be replaced by halogen, preferably chlorine or fluorine.

Furthermore, the definition that "[possible for] one or more, preferably up to three, nonadjacent saturated carbon units in the alkyl, alkenyl or alkynyl radicals mentioned to be replaced by a carbonyl group or by heteroatom units, such as oxygen, $S(O)_x$ where x=0, 1 or 2, $NR^6$ or $SiR^7R^8$, in which $R^6$ is hydrogen, $(C_1–C_4)$-alkyl, $(C_1–C_4)$-alkoxy or $(C_1–C_4)$-alkanoyl and $R^7$ and $R^8$ are $(C_1–C_4)$-alkyl, preferably methyl; and in which, furthermore, 3 to 12 atoms of these hydrocarbon radicals, which radicals are modified as above if desired, can form a ring and these hydrocarbon radicals, with or without the variations indicated, can if desired be substituted by one or more, preferably up to three—and in the case of fluorine up to the maximum number of—identical or different radicals from the series consisting of halogen, aryl, aryloxy, arylthio, cycloalkoxy, cycloalkylthio, heterocyclyl, heterocyclyloxy, heterocyclylthio, alkanoyl, cycloalkanoyl, haloalkanoyl, aroyl, arylalkanoyl, cycloalkylalkanoyl, heterocyclylalkanoyl, alkoxycarbonyl, haloalkoxycarbonyl, cycloalkoxycarbonyl, cycloalkylalkoxycarbonyl, arylalkoxycarbonyl, heterocyclylalkoxycarbonyl, aryloxycarbonyl, alkanoyloxy, haloalkanoyloxy, cycloalkanoyloxy, cycloalkylalkanoyloxy, aroyloxy, arylalkanoyloxy, heterocycloylalkanoyloxy, alkylsulfonyloxy, arylsulfonyloxy, hydroxyl, cyano, thiocyano or nitro, it being possible for the cycloaliphatic, aromatic or heterocyclic ring systems among the substituents just mentioned to be unsubstituted or substituted by up to three—and in the case of fluorine up to the maximum number of—identical or different substituents" means for example:

alkoxyalkyl radicals, for example the methoxymethyl, methoxyethyl or ethoxyethyl group; or alkoxyalkoxyalkyl radicals, for example the methoxy- or the ethoxyethoxyethyl group; or alkylthioalkyl radicals, for example the methyl- or the ethylthioethyl group; or alkylsulfinylalkyl radicals, for example the methyl- or ethylsulfinylethyl group; or alkylsulfonylalkyl radicals, for example the methyl- or ethylsulfonylethyl group; or alkyldialkylsilylalkyl, preferably alkyldimethylsilylalkyl, radicals, for example the trimethylsilylmethyl or the trimethylsilylethyl group; or trialkylsilyl, preferably alkyldimethylsilyl, radicals, for example the trimethylsilyl, ethyldimethylsilyl, tert-butyldimethylsilyl or the octyidimethylsilyl group; or cycloalkyldialkylsilyl, preferably cycloalkyldimethylsilyl, radicals, for example the cyclohexyldimethylsilyl group; or aryldialkylsilyl, preferably aryldimethylsilyl, radicals, for example the phenyldimethylsilyl group; or arylalkyldialkylsilyl, preferably aryldimethylsilyl, radicals, for example the benzyldimethylsilyl or the phenylethyldimethylsilyl group; or dimethylalkoxyalkylsilyl, for example the dimethylethoxypropylsilyl group;

alkanoylalkyl radicals, for example the acetylmethyl or the pivaloylmethyl group; or cycloalkanoylalkyl radicals, for example the cyclopropylcarbonylmethyl or the cyclohexylcarbonylmethyl group; or haloalkanoylalkyl radicals, for example the trifluoro- or trichloroacetylmethyl group; or aroylalkyl radicals, for example the benzoyl- or naphthoylalkyl radicals, for example the phenylacetylmethyl group; or heterocyclylcarbonylalkyl radicals, for example the thienyl- or pyridylacetylmethyl group; or arylalkyl radicals, for example the benzyl, the 2-phenylethyl, the 1-phenylethyl, the 1-methyl-1-phenylethyl group, the 3-phenylpropyl, the 4-phenylbutyl group, the 2-methyl-2-phenylethyl group or the 1-methyl- or 2-methylnaphthyl group; or heterocyclylalkyl radicals, for example the thienylmethyl, pyridylmethyl, furfuryl, tetrahydrofurfuryl, tetrahydropyranylmethyl or the 1,3-dioxolan-2-methyl group; or aryloxyalkyl radicals, for example the phenoxymethyl or naphthoxymethyl group; or cycloalkyl radicals, both monocyclic examples such as the cyclopropyl, cyclobutyl, cyclopentyl, cyclohexyl, cycloheptyl or cyclooctyl radical, or bicyclic radicals such as, for example, the norbornyl radical or the bicyclo[2.2.2]octane radical, or condensed radicals such as the decahydronaphthyl radical;

alkylcycloalkyl radicals, for example the 4-methyl- or tne 4-tert-butylcyclohexyl group or the 1-methylcyclopropyl, 1-methylcyclobutyl, 1-methylcyclopentyl or 1-methylcyclohexyl group;

cycloalkylalkyl radicals, for example the cyclohexylmethyl or cyclohexylethyl group;

or else haloalkyl derivatives of the corresponding groups, for example haloalkyl radicals, haloalkoxyalkyl radicals, alkoxyhaloalkyl radicals, haloalkylcycloalkyl radicals or halocycloalkyl radicals.

The explanation given above applies correspondingly to homologs and to radicals derived therefrom.

The present invention relates to compounds of the formula I in the form of the free base or an acid addition salt. Acids which can be used to form salts are inorganic acids, such as hydrochloric acid, hydrobromic acid, nitric acid, sulfuric acid or phosphoric acid, or organic acids, such as formic acid, acetic acid, propionic acid, malonic acid, oxalic acid, fumaric acid, adipic acid, stearic acid, oleic acid, methanesulfonic acid, benzenesulfonic acid or toluenesulfonic acid.

In addition to the abovementioned cis/trans isomerism about the cycloalkyl group, some of the compounds of the formula I have one or more asymmetric carbon atoms or stereoisomers on double bonds. Enantiomers or diastereomers may therefore occur. The invention embraces both the pure isomers and mixtures thereof. The mixtures of diastereomers can be separated into the components by customary methods, for example by selective crystallization from appropriate solvents or by chromatography. Racemates can be resolved into the enantiomers by customary methods, for example by forming a salt with an optically active acid, separating the diastereomeric salts and liberating the pure enantiomers by means of a base.

The invention additionally relates to a process for the preparation of compounds of the formula I, which comprises reacting a compound of the formula IV

in which A, $R^1$, $R^2$ and $R^3$ are as defined under formula I and L is a leaving group, for example halogen, alkylthio, alkanesulfonyloxy or arylsulfonyloxy, alkylsulfonyl or arylsulfonyl, with a nucleophile of the formula V

in which X, E and Q are as defined above for formula I and, if desired, subjecting the compounds of the formula I which have been obtained in this or a different manner to further derivatization at positions 5 or 6 of the pyrimidine system or, respectively, positions 2 and 3 of the pyridine system (radicals $R^2$ and $R^3$) or on the radical Q.

The above-described substitution reaction is known in principle. The leaving group L can be varied within wide limits and can, for example, be a halogen atom such as fluorine, chlorine, bromine or iodine, or alkylthio, such as methylthio or ethylthio, or alkanesulfonyloxy, such as methane-, trifluoromethane- or ethanesulfonyloxy, or arylsulfonyloxy, such as benzenesulfonyloxy or toluenesulfonyloxy, or alkylsulfonyl, such as methylsulfonyl or ethylsulfonyl, or arylsulfonyl, such as phenylsulfonyl or toluenesulfonyl.

The abovementioned reaction is carried out in a temperature range from 20° to 150° C., expediently in the presence of a base and, if appropriate, in an inert organic solvent, such as N,N-dimethylformamide, N,N-dimethylacetamide, dimethyl sulfoxide, N-methyl-2-pyrrolidinone, dioxane, tetrahydrofuran, 4-methyl-2-pentanone, methanol, ethanol, butanol, ethylene glycol, ethylene glycol dimethyl ether, toluene, chlorobenzene or xylene. Mixtures of the solvents mentioned can also be used.

If X is oxygen, examples of suitable bases are alkali metal or alkaline earth metal carbonates, hydrogen carbonates, amides or hydrides, such as sodium carbonate, sodium hydrogen carbonate, potassium carbonate, sodium amide or sodium hydride; if X is NH, suitable examples are alkali metal or alkaline earth metal carbonates, hydrogen carbonates, hydroxides, amides or hydrides, such as sodium carbonate, sodium hydrogen carbonate, potassium carbonate, sodium hydroxide, sodium amide or sodium hydride, or organic bases, such as triethylamine or pyridine. A second equivalent of an amine of the formula III can also be employed as auxiliary base.

The nucleophiles of the formula III which are required as starting materials can if X is oxygen be prepared by known methods, for example by reducing a carbonyl group with a suitable reducing agent, for example a complex metal hydride or else, in the case of an aldehyde or ketone, with hydrogen and a hydrogenation catalyst. To prepare the cis-cyclohexanols, the starting materials for the particularly preferred cis-cyclohexyloxy derivatives, the catalytic hydrogenation of suitably substituted phenols or the reduction of suitably substituted cyclohexanone derivatives using complex hydrides which carry sterically bulky substituents, for example L-Selectride®, is particularly appropriate.

The nucleophiles of the formula III which are required as starting materials can if X is NH be prepared by known methods, for example by reduction of an oxime, an azide or a nitrile with an appropriate reducing agent, for example a complex metal hydride or hydrogen in the presence of a hydrogenation catalyst, reductive amination or Leuckart-Wallach reaction of an aldehyde or ketone, or Gabriel reaction of an alkyl halide or alkyl tosylate. For the preparation of the cyclohexylamines, the starting materials for the particularly preferred cis-1,4-cyclohexylamino derivatives, the reductive amination of suitably substituted cyclohexanones with ammonium salts and sodium cyanoborohydride or with ammonia and hydrogen in the presence of metal catalysts, such as nickel, ruthenium, rhodium or palladium, the proportion of desired cis-amine being particularly high in the case of this method, is appropriate. A further method is the hydrogenation of anilines in the presence of hydrogenation catalysts.

The invention furthermore relates to a process for the preparation of compounds of the formula VI

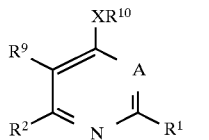

(VI)

in which $R^1$, $R^2$ and X are as defined above for formula I and, if $R^9$ is $(C_1-C_4)$-alkoxy, $R^2$ can also be $(C_1-C_4)$-alkyl, A is nitrogen $R^9$ is $(C_1-C_4)$-perfluoroalkyl, trifluoromethylthio, cyano or $(C_1-C_4)$-alkoxy $R^{10}$ is the unit EQ from formula I and, furthermore, is a $(C_1-C_{20})$-alkyl radical in which one or more, preferably up to three, nonadjacent saturated carbon units can be replaced by heteroatom units, such as oxygen, $S(O)_x$ where x=0, 1 or 2, $NR^{6'}$ or $SiR^{7'}R^{8'}$, where $R^{6'}$ is hydrogen, $(C_1-C_4)$-alkyl, $(C_1-C_4)$-alkanoyl or $(C_1-C_4)$-alkoxy, and where $R^{7'}$ and $R^{8'}$ are $(C_1-C_4)$-alkyl, and in which furthermore these alkyl radicals, with or without the variations indicated, can if desired be substituted by one or more, preferably up to three—and in the case of halogen up to the maximum number of—identical or different radicals from the series consisting of halogen, aryl, aryloxy, arylthio, cycloalkoxy, cycloalkylthio, heterocyclyl, heterocyclyloxy, heterocyclylthio, alkanoyl, cycloalkanoyl, haloalkanoyl, aroyl, arylalkanoyl, cycloalkylalkanoyl, heterocyclylalkanoyl, alkoxycarbonyl, haloalkoxycarbonyl, cycloalkoxycarbonyl, cycloalkylalkoxycarbonyl, arylalkoxycarbonyl, heterocyclylalkoxycarbonyl, aryloxycarbonyl, heterocyclyloxycarbonyl, alkanoyloxy, haloalkanoyloxy, cycloalkanoyloxy, cycloalkylalkanoyloxy, aroyloxy, arylalkanoyloxy, heterocycloylalkanoyloxy, alkylsulfonyloxy, arylsulfonyloxy, hydroxyl, cyano, thiocyano or nitro, it being possible for the cycloaliphatic, aromatic or heterocyclic ring systems among the substituents just mentioned to be unsubstituted or substituted by up to three—and in the case of fluorine up to the maximum number of—identical or different substituents, which comprises reacting a compound of the formula VII

(VII)

for which $R^1$, $R^2$, A, X and $R^{10}$ are as defined for formula VI and, if $R^9$ is $(C_1-C_4)$-alkoxy, $R^2$ can also be $(C_1-C_4)$-alkyl, and L is a leaving group which is as defined for formula IV, preferably bromine or iodine, with a compound $MR^9$, preferably in the presence of a copper(I) salt, where M is an alkali metal or alkaline earth metal and the copper(I) salt used is for example copper(I) chloride, bromide or iodide, or reacting the radical $R^9$ in the form of the copper(I) salt.

The reactions are carried out in an inert organic solvent or else in bulk in a temperature range from 80° to 250° C., preferably from 70° to 200° C.

The compounds of the formula VI for which $R^9$ is alkoxy are expediently prepared by reacting the compound $MR^9$, preferably the sodium or potassium salt, in an inert organic solvent, for example isopropanol, dimethylformamide, dimethylacetamide, N-methylpyrrolidone, 1,3-dimethyltetrahydro-2-(1H)-pyrimidinone, or else in the very alcohol on which the radical $R^9$ is based, with the compound of the formula VII, preferably in the presence of a copper(I) salt and, if desired, of an aliphatic carboxylic ester, preferably ethyl acetate.

The compounds of the formula VI for which $R^9$ is perfluoroalkyl, trifluoromethylthio or cyano are expediently prepared by reacting the copper(I) salts of the radicals $R^9$ in an inert organic solvent, for example dimethylformamide, dimethylacetamide, N-methylpyrrolidinone, 1,3-dimethyltetrahydro-2-(1H)-pyrimidinone or hexamethylphosphoric triamide, or else in bulk, with a compound of the formula VII, in a temperature range from 50° to 250° C., preferably from 100° to 200° C. A method of preparing compounds of the formula VI for which $R^9$ is cyano from a starting material of the formula VII for which L is iodine has been described (WO 93/22291). The process described therein, however, requires the use of a costly palladium reagent, whereas in the process claimed above inexpensive copper(I) cyanide is employed.

The starting materials of the formula VII for which L is iodine can be prepared by analogy with EP-A-470 600.

The preparation of the starting materials $R^9Cu$ is known from the literature (cf. e.g. J. C. S. Perkin I, 1980, 2755; Synthesis, 1975, 721).

The compounds of the formula VI, synthesized by the method described above, for which $R^{10}$ is a $(C_1-C_{20})$-alkyl radical in which one or more, preferably up to three, nonadjacent saturated carbon units can be replaced by heteroatom units, such as oxygen, $S(O)_x$ where x=0, 1 or 2, $NR^{6'}$ or $SiR^{7'}R^{8'}$, where $R^{6'}$ is hydrogen, $(C_1-C_4)$-alkyl, $(C_1-C_4)$-alkanoyl or $(C_1-C_4)$-alkoxy, and where $R^{7'}$ and $R^{8'}$ are $(C_1-C_4)$-alkyl, and in which furthermore these alkyl radicals, with or without the variations indicated, can if desired be substituted by one or more, preferably up to three—and in the case of halogen up to the maximum number of—identical or different radicals from the series consisting of halogen, aryl, aryloxy, arylthio, cycloalkoxy, cycloalkylthio, heterocyclyl, heterocyclyloxy, heterocyclylthio, alkanoyl, cycloalkanoyl, haloalkanoyl, aroyl, arylalkanoyl, cycloalkylalkanoyl, heterocyclylalkanoyl, alkoxycarbonyl, haloalkoxycarbonyl, cycloalkoxycarbonyl, cycloalkylalkoxycarbonyl, arylalkoxycarbonyl, heterocyclylalkoxycarbonyl, aryloxycarbonyl, heterocyclyloxycarbonyl, alkanoyloxy, haloalkanoyloxy, cycloalkanoyloxy, cycloalkylalkanoyloxy, aroyloxy, arylalkanoyloxy, heterocycloylalkanoyloxy, alkylsulfonyloxy, arylsulfonyloxy, hydroxyl, cyano, thiocyano or nitro, it being possible for the cycloaliphatic, aromatic or heterocyclic ring systems among the substituents just mentioned to be unsubstituted or to be substituted by up to three—and in the case of fluorine up to the maximum number of—identical or different substituents, also exhibit very good insecticidal, acaricidal, ixodicidal and fungicidal action. The invention therefore additionally relates to compounds of the formula VI for which $R^1$, $R^2$, $R^9$, A and X are as defined for formula VI and $R^{10}$ is $(C_1-C_{20})$-alkyl and, in this alkyl radical, one or more, preferably up to three, nonadjacent saturated carbon units can be replaced by a carbonyl group or by heteroatom units, such as oxygen, $S(O)_x$ where x=0, 1 or 2, $NR^{6'}$ or $SiR^{7'}R^{8'}$, where $R^{6'}$, $R^{7'}$ and $R^{8'}$ are as defined above for formula VI, and this hydrocarbon radical, with or without the variations indicated, can if desired be substituted by one or more, preferably up to three—and in the case of halogen up to the maximum number of—identical or different radicals from the series consisting of halogen, cycloalkyl, cycloalkoxy, aryloxy, arylthio, heterocyclyl, heterocyclyloxy, heterocyclylthio, alkanoyl, cycloalkanoyl, haloalkanoyl, aroyl, arylalkanoyl, cycloalkylalkanoyl, heterocyclylalkanoyl, alkoxycarbonyl, haloalkoxycarbonyl, cycloalkoxycarbonyl, cycloalkylalkoxycarbonyl, arylalkoxycarbonyl, heterocyclylalkoxycarbonyl, aryloxycarbonyl, heterocyclyloxycarbonyl, alkanoyloxy, haloalkanoyloxy, cycloalkanoyloxy, cycloalkylalkanoyloxy, aroyloxy, arylalkanoyloxy, heterocycloalkanoyloxy, alkylsulfonyloxy, arylsulfonyloxy, hydroxyl, cyano, thiocyano or nitro, it being possible for the cycloaliphatic, aromatic or heterocyclic ring systems among the substituents just mentioned to be unsubstituted or to be substituted by up to three—and in the case of fluorine up to the maximum number of—identical or different substituents, in particular those compounds of the formula VI for which $R^{10}$ is $(C_1-C_{20})$-alkyl, preferably $(C_4-C_{15})$-alkyl, aryl-$(C_1-C_4)$-alkyl, phenoxyphenyl-$(C_1-C_4)$-alkyl, in which the aryl group or the phenoxy group is unsubstituted or is substituted by one, two or three substituents which are identical or different and are in each case halogen, $(C_1-C_4)$-alkyl, $(C_1-C_4)$-haloalkyl, $(C_1-C_4)$-alkoxy, $(C_1-C_4)$-haloalkoxy or $(C_1-C_4)$-alkoxy-$(C_1-C_4)$-alkyl.

Examples of further methods of preparing compounds of the formula I are

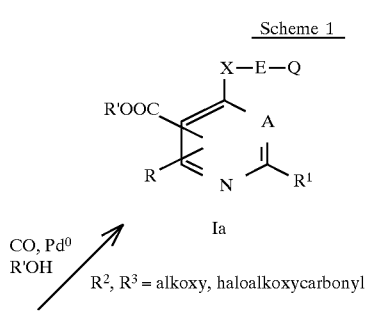

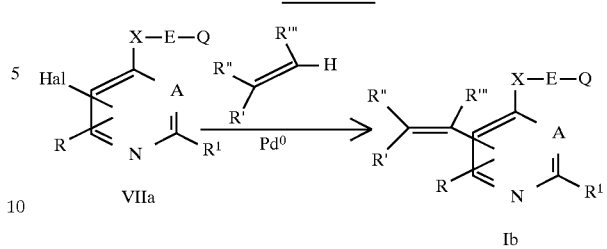

Hal = Br, I    $R^2$, $R^3$ = alkynyl, haloalkenyl

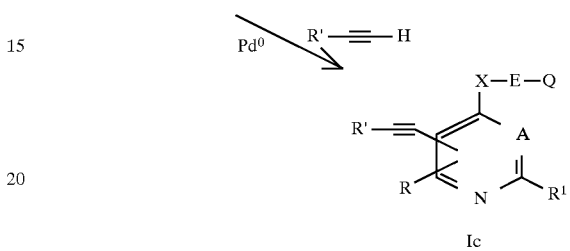

$R^2$, $R^3$ = alkynyl, haloalkynyl, silylalkynyl

Regarding the above reactions: L. S. Hegedus in Organometallic Synthesis, ed. M. Schlosser, Wiley, Chichester 1994.

The compounds of the formula Ic for which R' is hydrogen are expediently prepared by reacting the compounds VIIa with a silyl-protected acetylene, preferably trimethylsilylacetylene, and eliminating the silyl group from the product Ic for which R' is, for example, trimethylsilyl, using hydroxide or fluoride.

The compounds obtained according to Scheme 1 can be subjected to further derivatization:

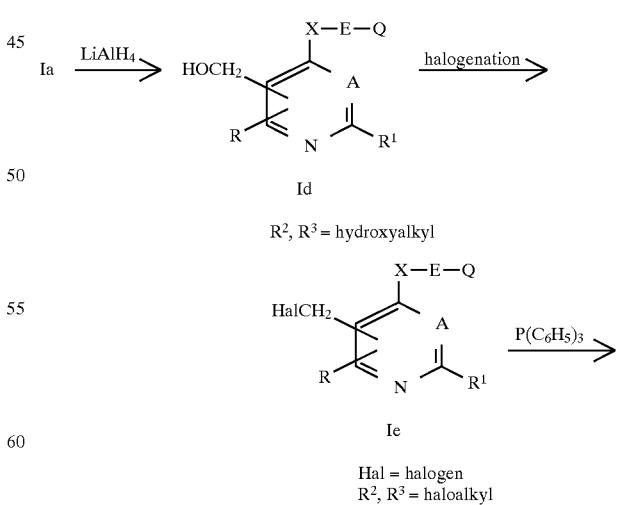

Hal = halogen
$R^2$, $R^3$ = haloalkyl

Examples of halogenating agents are $SOCl_2$, HBr, HI, DAST

Scheme 2

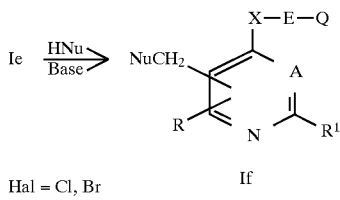

Hal = Cl, Br
Nu = Cn⁻, CR⁻, SR⁻
$R^2, R^3$ = cyanoalkyl, alkoxyalkyl, alkylthioalkyl The alcohol Id can be oxidized by various methods (Swern, Pfitzner-Moffat or $CrO_3$ oxidation) to the aldehyde Ig, from which in turn alkenyl or haloalkenyl derivatives Ib can be obtained by Wittig reaction (cf. Houben-Weyl, E1, Organic phosphorus compounds, p. 720).

Scheme 3

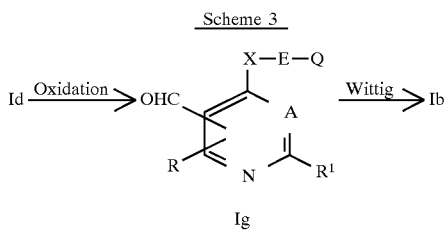

$R^2, R^3$ = $C_1$-alkanoyl

Addition of halogen onto the alkenyl derivatives Ib and the alkynyl derivatives Ic leads respectively to haloalkyl or haloalkenyl derivatives. Hydrogen halide can be eliminated from the former using bases to give haloalkenyl derivatives.

The alkynyl derivatives Ic for which R' is hydrogen can be further modified in accordance with Scheme 4:

Scheme 4

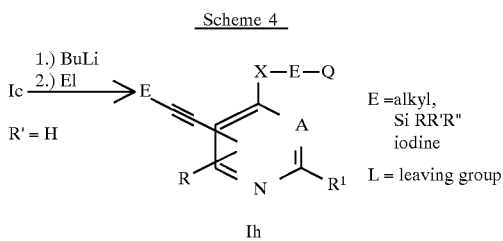

E = alkyl, Si RR'R" iodine
L = leaving group

Regarding the preparation of the iodoalkynyl derivatives: Houben-Weyl, Volume 5/2a, 604.

The alkynyl derivatives Ic for which R' is alkyl or hydrogen can be further modified in accordance with Scheme 5:

Scheme 5

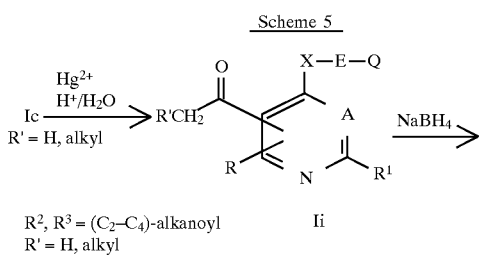

$R^2, R^3$ = $(C_2$–$C_4)$-alkanoyl
R' = H, alkyl

-continued
Scheme 5

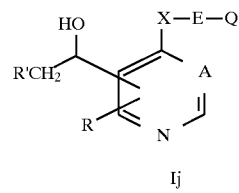

$R^2, R^3$ = $(C_2$–$C_4)$-hydroxyalkyl
R' = H, alkyl

In analogy with Scheme 2, the compounds Ij can be reacted further to give (1-haloalkyl)-, (1-cyanoalkyl)-, (1-alkoxyalkyl)- and (1-alkylthioalkyl)- derivatives.

Alternatively, the compounds Ii and Ij can be prepared as follows:

Scheme 6

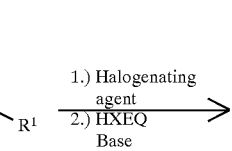

R' - H, alkyl
L = leaving group
Oxidizing agent

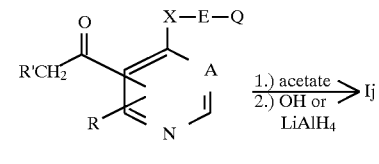

$R^2, R^3$ = haloalkyl
R' = H, alkyl

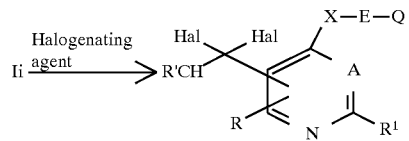

Using appropriate halogenating agents, the carbonyl derivatives Ig and Ii can be converted into geminal dihalo compounds.

| Scheme 7 | R' = H, alkyl |
|---|---|
| | $R^2, R^3$ = haloalkyl, Hal = F, Cl |

Examples of suitable halogenating agents are $SF_4$, DAST or $PCl_5$ (Cf. J. Org. Chem. 40, 574 (1975), Org. React. 21, 1 (1974), J. Chem. Soc. 1958, 3742).

Alkenyl derivatives Ib, furthermore, can be obtained by elimination reactions from suitably substituted precursors I' or I":

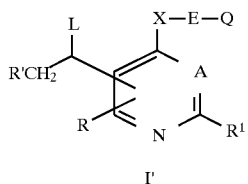

I'

R' = H, alkyl

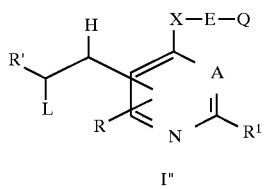

I"

R' = H, alkyl

L is a leaving group, for example halogen, hydroxyl or alkyl- or arylsulfinyl. It is eliminated under basic (where L=halogen) or acidic (where L=OH) conditions or thermally (where L=alkyl- or arylsulfinyl). Precursors I' with L α to the heterocycle are, for example, the compounds Ij and Ik and the sulfoxide derivatives which are obtainable from Ik by reaction with alkane- or arenethiols followed by per-acid oxidation. Precursors I" with L β to the heterocycle can be prepared, for the particularly preferred pyrimidine derivatives, for example, as follows (Scheme 8, Scheme 9):

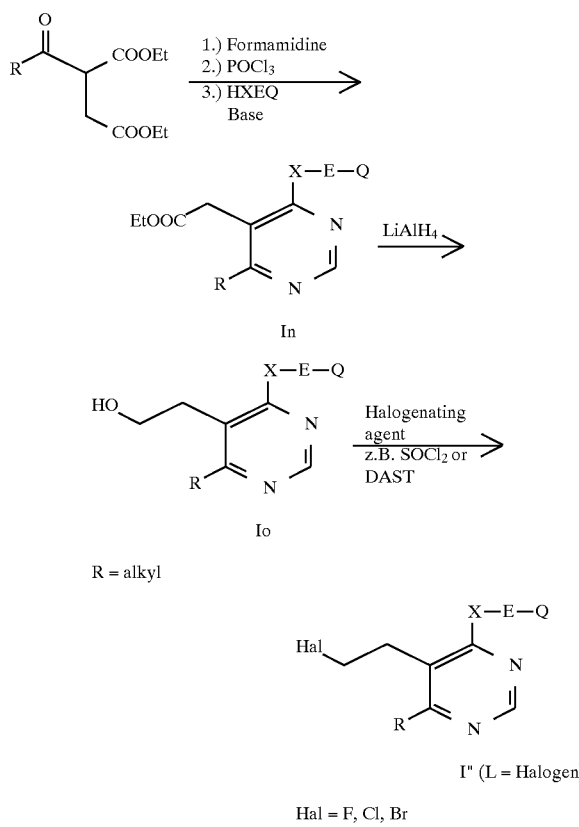

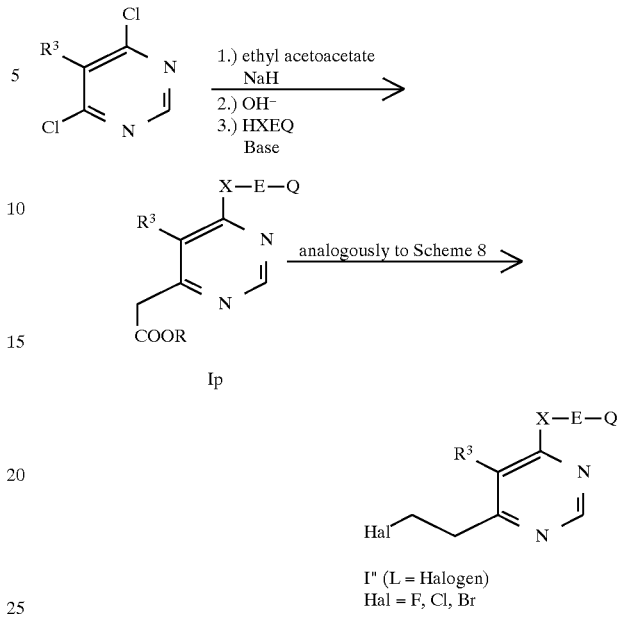

While being tolerated well by plants and having favorable toxicity toward warm-blooded animals, the active substances are suitable for controlling animal pests, especially insects, arachnids, helminths and molluscs, and very preferably for controlling insects and arachnids, which are encountered in agriculture, in animal breeding, in forestry, in the protection of stored products and materials, and in the hygiene sector. They are active against normally sensitive and resistant species and against all or certain stages of development. The abovementioned pests include:

From the order of the Acarina, for example, *Acarus siro, Argas spp., Ornithodoros spp., Dermanyssus gallinae, Eriophyes ribis, Phyllocoptruta oleivora, Boophilus spp., Rhipicephalus spp., Amblyomma spp., Hyalomma spp., Ixodes spp., Psoroptes spp., Chorioptes spp., Sarcoptes spp., Tarsonemus spp., Bryobia praetiosa, Panonychus spp., Tetranychus spp., Eotetranychus spp., Oligonychus spp.* and *Eutetranychus spp.*.

From the order of the Isopoda, for example, *Oniscus asellus, Armadium vulgar* and *Porcellio scaber.* From the order of the Diplopoda, for example, *Blaniulus guttulatus.*

From the order of the Chilopoda, for example, *Geophilus carpophagus* and *Scutigera spp.*

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea madeirae, Blattella germanica, Acheta domesticus, Gryllotalpa spp., Locusta migratoria migratorioides, Melanoplus differentialis* and *Schistocerca gregaria.*

From the order of the Isoptera, for example, *Reticulitermes spp.*.

From the order of the Anoplura, for example, *Phylloera vastatrix, Pemphigus spp., Pediculus humanus corporis, Haematopinus spp.* and *Linognathus spp.*.

From the order of the Mallophaga, for example, *Trichodectes spp.* and *Damalinea spp.*.

From the order of the Thysanoptera, for example, *Hercinothrips femoralis* and *Thrips tabaci*.

From the order of the Heteroptera, for example, *Eurygaster spp., Dysdercus intermedius, Piesma quadrata, Cimex lectularius, Rhodnius prolixus* and *Triatoma spp.*. From the order of the Homoptera, for example, *Aleurodes brassicae, Bemisia tabaci, Trialeurodes vaporariorum, Aphis gossypii, Bravicoryne brassicae, Cryptomyzus ribis, Doralis fabae, Doralis pomi, Eriosoma lanigerum, Hyalopterus arundinis, Macrosiphum avenae, Myzus spp., Phorodon humuli, Rhopalosiphum padi, Empoasca spp., Euscelus bilobatus, Nephotettix cincticeps, Lecanium corni, Saissetia oleae, Laodelphax striatellus, Nilaparvata lugens, Aonidiella aurantii, Aspidiotus hederae, Pseudococcus spp.* and *Psylla spp.*.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria spp., Bucculatrix thurberiella, Phyllocnistis citrella, Agrotis spp., Euxoa spp., Feltia spp., Earias insulana, Heliothis spp., Laphygma exigua, Mamestra brassicae, Panolis flammea, Prodenia litura, Spodoptera spp., Trichoplusia ni, Carpocapsa pomonella, Pieris spp., Chilo spp., Pyrausta nubilalis, Ephestia kuehniella, Galleria mellonella, Cacoecia podana, Capua reticulana, Choristoneura fumiferana, Clysia ambiguella, Homona magnanima* and *Tortrix viridana*.

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica spp., Psylloides chrysocephala, Epilachna varivestis, Atomaria spp., Oryzaephilus surinamensis, Anthonomus spp., Sitophilus spp., Otiorrhynchus sulcatus, Cosmopolites sordidus, Ceuthorrhynchus assimilis, Hypera postica, Dermestes spp., Trogoderma spp., Anthrenus spp., Attagenus spp., Lyctus spp., Meligethes aeneus, Ptinus spp., Niptus hololeucus, Gibbium psylloides, Tribolium spp., Tenebrio molitor, Agriotes spp., Conoderus spp., Melolontha melolontha, Amphimallon solstitialis* and *Costelytra zealandica*.

From the order of the Hymenoptera, for example, *Diprion spp., Hoplocampa spp., Lasius spp., Monomorium pharaonis* and *Vespa spp.*.

From the order of the Diptera, for example, *Aedes spp., Anopheles spp., Culex spp., Drosophila melanogaster, Musca spp., Fannia spp., Calliphora erythrocephala, Lucilia spp., Chrysomyia spp., Cuterebra spp., Gastrophilus spp., Hyppobosca spp., Stomoxys spp., Oestrus spp., Hypoderma spp., Tabanus spp., Tannia spp., Bibio hortulanus, Oscinella frit, Phorbia spp., Pegomyia hyoscyami, Ceratitis capitata, Dacus oleae* and *Tipula paludosa*.

From the order of the Siphonaptera, for example, *Xenopsylla cheopsis* and *Ceratophyllus spp.*.

From the order of the Arachnida, for example, *Scorpio maurus* and *Latrodectus mactans.*

From the class of the helminths, for example, Haemonchus, Trichostrongulus, Ostertagia, Cooperia, Chabertia, Strongyloides, Oesophagostomum, Hyostrongulus, Ancylostoma, Ascaris and Heterakis and also Fasciola.

From the class of the Gastropoda, for example, *Deroceras spp., Arion spp., Lymnaea spp., Galba spp., Succinea spp., Biomphalaria spp., Bulinus spp.* and *Oncomelania spp.*.

From the class of the Bivalva, for example, *Dreissena spp.*.

The plant-parasitic nematodes which can be controlled in accordance with the invention include, for example, the root-parasitic soil nematodes such as, for example, those of the genera Meloidogyne (root knot eelworms, such as *Meloidogyne incognita, Meloidogyne hapla* and *Meloidogyne javanica*), Heterodera and Globodera (cyst nematodes, such as *Globodera rostochiensis, Globodera pallida, Heterodera trifolii*) and of the genera Radopholus, such as *Radopholus similis*, Pratylenchus, such as *Pratylenchus neglectus, Pratylenchus penetrans* and *Pratylenchus curvitatus;*

Tylenchulus, such as *Tylenchulus semipenetrans,* Tylenchorhynchus, such as *Tylenchorhynchus dubius* and *Tylenchorhynchus claytoni*, Rotylenchus such as *Rotylenchus robustus,* Helicotylenchus, such as *Helicotylenchus multicinctus,* Belonoaimus, such as *Belonoaimus longicaudatus,* Longidorus, such as *Longidorus elongatus,* Trichodorus, such as *Trichodorus primitivus,* and Xiphinema, such as Xiphinema index.

The compounds according to the invention can also be used to control the nematode genera Ditylenchus (stem parasites, such as *Ditylenchus dipsaci* and *Ditylenchus destructor*), Aphelenchoides (leaf nematodes, such as *Aphelenchoides ritzemabosi*) and Anguina (leaf-gall nematodes, such as *Anguina tritici*).

The invention also relates to compositions, especially insecticidal and acaricidal compositions, which comprise the compounds of the formula I in addition to suitable formulation auxiliaries.

The compositions according to the invention comprise the active substances of the formulae I in general in a proportion of from 1 to 95% by weight.

They can be formulated in various ways depending on the biological and/or chemicophysical parameters which prevail. Possible formulations which are suitable are therefore: wettable powders (WP), emulsifiable concentrates (EC), aqueous solutions (SL), emulsions, sprayable solutions, oil- or water-based dispersions (SC), suspoemulsions (SE), dusts (DP), seed-dressing products, granules in the form of microgranules, spray granules, coated granules and adsorption granules, water-dispersible granules (WG), ULV formulations, microcapsules, waxes or baits.

These individual types of formulation are known in principle and are described, for example, in:

Winnacker-Küchler, "Chemische Technologie" [Chemical Technology], Volume 7, C. Hauser Verlag Munich, 4th ed. 1986; van Falkenberg, "Pesticides Formulations", Marcel Dekker N.Y., 2nd ed. 1972–73; K. Martens, "Spray Drying Handbook", 3rd ed. 1979, G. Goodwin Ltd. London.

The formulation auxiliaries required, such as inert materials, surfactants, solvents and other additives, are likewise known and are described, for example, in:

Watkins, "Handbook of Insecticide Dust Diluents and Carriers", 2nd ed., Darland Books, Caldwell N.J.; H. v. Olphen, "Introduction to Clay Colloid Chemistry", 2nd ed., J. Wiley & Sons, N.Y.; Marsden, "Solvents Guide", 2nd ed., Interscience, N.Y. 1950; McCutcheon's, "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-Active Ethylene oxide adducts], Wiss. Verlagsgesell., Stuttgart 1967; Winnacker-Küchler, "Chemische Technologie", Volume 7, C. Hauser Verlag Munich, 4th ed. 1986.

Based on these formulations, it is also possible to produce combinations with other pesticidally active substances, fertilizers and/or growth regulators, for example in the form of a readymix or a tank mix. Wettable powders are preparations, uniformly dispersible in water, which contain, beside the active substance and in addition to a diluent or inert material, wetting agents, for example polyoxethylated alkylphenols, polyoxethylated fatty alcohols, alkyl- or alkylphenolsulfonates, and dispersing agents, for example sodium ligninsulfonate or sodium 2,2'-dinaphthylmethane-6,6'-disulfonate. Emulsifiable concentrates are prepared by dissolving the active substance in an organic solvent, for example butanol, cyclohexanone, dimethylformamide, xylene or higher-boiling aromatics or hydrocarbons, with addition of one or more emulsifiers. As emulsifiers, the following can be used, for example: calcium salts of alkylarylsulfonates, such as Ca dodecylbenzenesulfonate, or nonionic emulsifiers such as fatty acid polyglycol esters, alkylaryl polyglycol ethers, fatty alcohol polyglycol ethers, propylene oxide/ethylene oxide condensation products, alkyl polyethers, sorbitan fatty acid esters, polyoxyethylene sorbitan fatty acid esters or polyoxethylene sorbitol esters.

Dusting agents are obtained by grinding the active substance with finely divided solid substances, for example talc, natural clays such as kaolin, bentonite, poryphillite or diatomaceous earth. Granules can be prepared either by atomizing the active substance onto adsorptive, granulated inert material or by applying active substance concentrates onto the surface of carrier materials such as sand or kaolinites, or of granulated inert material, by means of adhesives, for example polyvinyl alcohol or sodium polyacrylate, or alternatively mineral oils. Suitable active substances can also be granulated in the fashion conventional for the preparation of fertilizer granules, if desired as a mixture with fertilizers.

In wettable powders, the concentration of active substance is, for example, from approximately 10 to 90% by weight, the remainder to 100% by weight being composed of customary formulation components. In the case of emulsifiable concentrates, the concentration of active substance may be from approximately 5 to 80% by weight. Formulations in dust form comprise in most cases from 5 to 20% by weight of active substance, sprayable solutions from about 2 to 20% by weight. In the case of granules, the content of active substance depends partly on whether the active compound is in liquid or solid form and on which granulation auxiliaries, fillers, etc. are being used.

In addition, the abovementioned formulations of active substance comprise, if appropriate, the adhesives, wetting agents, dispersants, emulsifiers, penetrants, solvents, fillers or carriers which are customary in each case.

The concentrates, which are in the commercially customary form, are if appropriate diluted in the customary manner for their use, for example using water in the case of wettable powders, emulsifiable concentrates, dispersions and some microgranules. Dust and granule preparations, and also sprayable solutions, are normally not diluted any further with other inert substances before being used.

The application rate required varies with the external conditions, such as temperature and humidity among others. It can fluctuate within wide limits, for example between 0.0005 and 10.0 kg/ha or more of active substance, but is preferably between 0.001 and 5 kg/ha.

The active substances according to the invention may be present in their commercially customary formulations, and in the application forms prepared from these formulations, as mixtures with other active substances, such as insecticides, attractants, sterilants, acaricides, nematicides, fungicides, growth regulators or herbicides.

The pesticides include, for example, phosphates, carbamates, carboxylates, formamidines, tin compounds and substances produced by microorganisms, inter alia.

Preferred mixture components are 1. from the group of the phosphorus compounds acephate, azamethiphos, azinphosethyl, azinphosmethyl, bromophos, bromophos-ethyl, chlorfenvinphos, chlormephos, chlorpyrifos, chlorpyrifosmethyl, demeton, demeton-S-methyl, demeton-S-methylsulphone, dialifos, diazinon, dichlorvos, dicrotophos, O,O-1,2,2,2-tetrachloroethyl phosphorothioate (SD 208 304), dimethoate, disulfoton, EPN, ethion, ethoprophos, etrimfos, famphur, fenamiphos, fenitriothion, fensulfothion, fenthion, fonofos, formothion, heptenophos, isozophos, isothioate, isoxathion, malathion, methacrifos, methamidophos, methidathion, salithion, mevinphos, monocrotophos, naled, omethoate, oxydemeton-methyl, parathion, parathionmethyl, phenthoate phorate, phosalone, phosfolan, phosmet, phosphamidon, phoxim, pirimiphos, pirimiphosethyl, pirimiphosmethyl, profenofos, propaphos, proetamphos, prothiofos, pyraclofos, pyridapenthion, quinalphos, sulprofos, temephos, terbufos, tetraclorvinphos, thiometon, triazophos, trichlorphon, vamidothion;

2. from the group of the carbamates aldicarb, 2-sec-butylphenyl methylcarbamate (BPMC), carbaryl, carbofuran, carbosulfan, cloethocarb, benfuracarb, ethiefencarb, furathiocarb, isoprocarb, methomyl, 5-methyl-m-cumenylbutyryl (methyl)carbamate, oxamyl, pirimicarb, propoxur, thiodicarb, thiofanox, ethyl 4,6,9-triaza-4-benzyl-6,10-dimethyl-8-oxa-7-oxo-5,11-dithia-9-dodecenoate (OK 135), 1-methylthio(ethylideneamino)-N-methyl-N-(morpholinothio)carbamate (UC 51717);

3. from the group comprising the carboxylates allethrin, alphametrin, 5-benzyl-3-furylmethyl (E)-(1R) cis-2,2-dimethyl-3-(2-oxothiolan-3-ylidenemethyl) cyclopropanecarboxylate, bioallethrin, bioallethrin ((S) cyclopentyl isomer), bioresmethrin, biphenate, (RS)-1-cyano-1-(6-phenoxy-2-pyridyl)methyl (1RS)-trans-3-(4-tert-butyl-phenyl)-2,2-dimethylcyclopropanecarboxylate (NCI 85193), cycloprothrin, cyhalothrin, cythithrin, cypermethrin, cyphenothrin, deltamethrin, empenthrin, esfenvalerate, fenfluthrin, fenpropathrin, fenvalerate, flucythrinate, flumethrin, fluvalinate (D-isomers), permethrin, phenothrin ((R)-isomers), d-prallethrin, pyrethrins (natural products), resmethrin, tefluthrin, tetramethrin, tralomethrin;

4. from the group of the amidines amitraz, chlordimeform;

5. from the group of the tin compounds cyhexatin, fenbutatin oxide;

6. others abamectin, Bacillus thuringiensis, bensultap, binapacryl, bromopropylate, buprofezin, camphechlor, cartap, chlorobenzilate, chlorfluazuron, 2-(4-chlorophenyl)-4,5-diphenylthiophene (UBI-T 930), clorfentezine, 2-naphthylmethyl cyclopropanecarboxylate (Ro 12-0470), cyromazin, N-(3,5-dichloro-4-(1,1,2,3,3,3-hexafluoro-1-propoxy)phenyl)carbamoyl)-2-chlorobenzocarboximide, DDT, dicofol, N-(N-(3,5-dichloro-4-(1,1,2,2-tetrafluoroethoxy)phenylamino)carbonyl)-2,6-difluorobenzamide (XRD 473), diflubenzuron, N-(2,3-dihydro-3-methyl-1,3-thiazol-2-ylidene)2,4-xylidine, dinobuton, dinocap, endosulfan, ethofenprox, (4-ethoxyphenyl)(dimethyl)(3-(3-phenoxyphenyl)-propyl) silane, (4-ethoxyphenyl)(3-(4-fluoro-3-phenoxyphenyl) propyl)dimethylsilane, fenoxycarb, 2-fluoro-5-(4-(4-ethoxyphenyl)-4-methyl-1-pentyl)diphenyl ether (MTI 800), granulosis and nuclear polyhedrosis viruses, fenthiocarb, flubenzimine, flucycloxuron, flufenoxuron, gamma-HCH, hexythiazox, hydramethyinon (AC 217300), ivermectin, 2-nitromethyl-4,5-dihydro-6H-thiazine (DS 52618), 2-nitromethyl-3,4-dihydrothiazole (SD 35651), 2-nitromethylene-1,2-thiazinan-3-ylcarbamaldehyde (WL 108477), propargite, teflubenzuron, tetradifon, tetrasul, thiocyclam, trifumuron and imidacloprid.

The active substance content of the use forms prepared from the commercially customary formulations can be from 0.00000001 to 95% by weight of active substance, preferably between 0.00001 and 1% by weight.

Application is effected in a conventional fashion, matched to the use forms.

The active substances according to the invention are also suitable for controlling ecto- and endoparasites in the veterinary sector or in the sector of animal husbandry.

The active substances according to the invention are in this case applied in a known fashion, such as by oral application in the form of, for example, tablets, capsules, potions or granules, by dermal application in the form of, for example, dipping, spraying, pouring-on and spotting-on and powdering, and also by parenteral application in the form of, for example, injection.

The novel compounds, according to the invention, of the formula I can accordingly also be employed particularly advantageously in livestock husbandry (for example cattle, sheep, pigs and poultry such as chickens, geese etc.). In a preferred embodiment of the invention, the novel compounds, if appropriate in suitable formulations (cf. above) and if appropriate with the drinking water or feed, are administered orally to the animals. Since excretion in the droppings occurs in an effective fashion, the development of insects in the animal droppings can be prevented very simply in this fashion. The dosages and formulations suitable in each case are particularly dependent on the type and stage of development of the productive animals and also on the degree of infestation, and can easily be determined and fixed by conventional methods. In the case of cattle, the novel compounds can be employed, for example, in dosages of 0.01 to 1 mg/kg of body weight.

The compounds of the formula I according to the invention are also distinguished by an outstanding fungicidal action. Fungal pathogens which have already penetrated the plant tissue can be successfully subjected to curative control. This is particularly important and advantageous in the case of those fungal diseases which can no longer be controlled effectively with the otherwise customary fungicides when infection has taken place already. The spectrum of action of the claimed compounds embraces various economically important phytopathogenic fungi, for example *Plasmopara viticola, Phytophthora infestans, Erysiphe graminis, Piricularia oryzae, Pyrenophora teres, Leptosphaeria nodorum, Pellicularia sasakii* and *Puccinia recondite*.

In addition, the compounds according to the invention are also suitable for use in technical fields, for example as wood preservatives, as preservatives in paints, in cooling lubricants for metalworking, or as preservatives in drilling and cutting oils.

The active substances according to the invention in their commercially customary formulations can be employed either alone or in combination with other fungicides known from the literature.

Examples of fungicides which are known from the literature and which can be combined, in accordance with the invention, with the compounds of the formula I are the following products: aldimorph, andoprim, anilazine, BAS 480F, BAS 450F, BAS 490F, benalaxyl, benodanil, benomyl, binapacryl, bitertanol, bromuconazole, buthiobate, captafol, captan, carbendazim, carboxin, CGA 173506, cyprodinil, cyprofuram, dichlofluanid, dichlomezin, diclobutrazol, diethofencarb, difenconazol (CGA 169374), difluconazole, dimethirimol, dimethomorph, diniconazole, dinocap, dithianon, dodemorph, dodine, edifenfos, ethirimol, etridiazole, epoxiconazole, fenbuconazole, fenarimol, fenfuram, fenpiclonil, fenpropidin, fenpropimorph, fentin acetate, fentin hydroxide, ferimzone (TF164), fluazinam, fluobenzimine, fludioxinil, fluquinconazole, fluorimide, flusilazole, flutolanil, flutriafol, folpet, fosetylaluminium, fuberidazole, fulsulfamide (MT-F 651), furalaxyl, furconazole, furmecyclox, guazatine, hexaconazole, ICI A5504, imazalil, imibenconazole, iprobenfos, iprodione, isoprothiolane, KNF 317, copper compounds, such as Cu oxychloride, oxine-Cu, Cu oxide, mancozeb, maneb, mepanipyrim (KIF 3535), metconazol, mepronil, metalaxyl, methasulfocarb, methfuroxam, MON 24000, myclobutanil, nabam, nitrothalidopropyl, nuarimol, ofurace, oxadixyl, oxycarboxin, penconazole, pencycuron, PP 969, probenazole, propineb, prochloraz, procymidon, propamocarb, propiconazole, prothiocarb, pyracarbolid, pyrazophos, pyrifenox, pyrimethanil, pyroquilon, rabenzazole, RH7592, sulfur, tebuconazole, TF 167, thiabendazole, thicyofen, thiofanatemethyl, thiram, tolclofos-methyl, tolylfluanid, triadimefon, triadimenol, triazoxid, tricyclazole, tridemorph, triflumizol, triforine, trifionazol, validamycin, vinchlozolin, XRD 563, zineb, sodium dodecyl-sulfonate, sodium dodecyl sulfate, sodium C13/C15 alcohol ether sulfonate, sodium cetostearyl phosphate ester, sodium dioctylsulfosuccinate, sodium isopropyinaphthalenesulfonate, sodium methylenebisnaphthalenesulfonate, cetyltrimethylammonium chloride, salts of long-chain primary, secondary or tertiary amines, alkylpropyleneamines, laurylpyrimidinium bromide, ethoxylated quaternized fatty arnines, alkyldimethylbenzylammonium chloride and 1-hydroxyethyl-2-alkylimidazoline.

The abovementioned components for combinations are known active substances of which many are described in Ch. R. Worthing, S. B. Walker, The Pesticide Manual, 7th edition (1983), British Crop Protection Council. The active substance content of the use forms prepared from commercially customary formulations can vary within wide limits, and the concentration of active substance in the use forms can be from 0.0001 up to 95% by weight of active substance, preferably between 0.0001 and 1% by weight. The formulations are applied in a customary manner adapted to suit the use forms.

The examples which follow illustrate the invention without limiting it thereto.

A. FORMULATION EXAMPLES a) A dusting agent is obtained by mixing 10 parts by weight of active substance and 90 parts by weight of talc as inert material and comminuting in a hammer mill.

b) A wettable powder which is easily dispersible in water is obtained by mixing 25 parts by weight of active substance, 65 parts by weight of kaolin-containing quartz as inert material, 10 parts by weight of potassium ligninsulfonate and 1 part by weight of sodium oleoylmethyltaurinate as wetting and dispersing agent, and grinding in a pinned disk mill.

c) A dispersion concentrate which is easily dispersible in water is prepared by mixing 40 parts by weight of active substance with 7 parts by weight of a sulfosuccinic monester, 2 parts by weight of a sodium ligninsulfonate and 51 parts by weight of water and grinding in a ball mill to a fineness of below 5 microns.

d An emulsifiable concentrate can be prepared from 15 parts by weight of active substance, 75 parts by weight of cyclohexane as solvent and 10 parts by weight of ethoxylated nonylphenol (10 EO) as emulsifier.

e) Granules can be prepared from 2 to 15 parts by weight of active substance and an inert granule carrier material such as attapulgite, granulated pumice and/or quartz sand. It is expedient to use a suspension of the wettable powder of Example b) with a solids content of 30% which is sprayed onto the surface of attapulgite granules which are then dried and intimately mixed. The proportion by weight of the wettable powder in this case is about 5% and that of the inert carrier material is about 95% of the finished granules.

B. PREPARATION EXAMPLES

Example 1

4-(cis-4-tert-Butylcyclohexylamino)-6-ethyl-5-iodopyrimidine 7.25 g (30 mmol) of 4-chloro-5-iodo-5-ethylpyrimidine (EP 470 600), 5.6 g (36 mmol) of cis-4-tert-butylcyclohexylamine and 6.1 g of triethylamine were heated at from 80° to 90° C. for 4 hours without solvent. After cooling, the mixture was taken up in water/toluene and the organic phase was dried and concentrated. The crude product was purified by chromatography on silica gel using petroleum ether/ethyl acetate (7:3), to give 7.4 g (56.7% of theory) of a yellow oil.

Example 2

4-(cis-4-tert-Butylcyclohexylamino)-5-cyano-6-ethylpyrimidine 1.8 g (5 mmol) of 4-(cis-4-tert-butylcyclohexylamino)-6-ethyl-5-iodopyrimidine (Example 1) and 1.0 g of copper(I) cyanide were stirred at 200° C. for 30 minutes without solvent. After cooling, the mixture was taken up in water/dichloromethane, the organic phase was again extracted by stirring with aqueous ammonia solution, and the extract was dried and concentrated. The crude product was purified by chromatography on silica gel using petroleum ether/ethyl acetate (7:3), to give 750 mg (52.4% of theory) of a colorless oil which crystallized on standing.

m.p.: 66° to 67° C.

Example 2a

5-Cyano-6-ethyl-4-[cis-4-(1,1,2-trimethylpropyl)cyclohexylamino]pyrimidine

Prepared as in Example 2 from 6-ethyl-5-iodo-4-[cis-4-(1,1,2-trimethylpropyl)cyclohexylamino]pyrimidine and copper(I) cyanide.

m.p.: 51° to 53° C.

Example 3

5-Ethoxycarbonyl-6-ethyl-4-(cis-4-trimethylsilylcyclohexylamino)pyrimidine 1.00 g (4.66 mmol) of 4-chloro-5-ethoxycarbonyl-6-ethylpyrimidine (EP 606 011), 0.84 g (4.89 mmol) of cis-4-trimethylsilylcyclohexylamine and 0.94 g (9.29 mmol) of triethylamine were heated at 70° C. for 5 hours without solvent. After cooling, the mixture was taken up in water/methyl chloride and the organic phase was dried and concentrated. The residue was purified by chromatography on silica gel using petroleum ether/ethyl acetate (4:1), to give 1.1 g (67% of theory) of a colorless oil.

Preparation of the starting material cis-4-trimethylsilylcyclohexylamine

A solution of 18.0 g (106 mmol) of 4-trimethylsilylcyclohexanone (prepared according to R. J. Fessenden, K. Seeler, M. Dagani, J. Org. Chem. 1966, 31, 2483) in 120 ml of ammoniacal isopropanol (90 g/l) was hydrogenated at 50° C. and 50 bar for 20 hours over 2 g of 5% Pd/Rh (4:1) on active charcoal (Degussa). For working up, the catalyst was filtered off and the solvent was removed, to give 15.9 g (93 mmol, 88%) of a colorless oil which was used subsequently without further purification.

Example 4

4-(cis-4-tert-Butylcyclohexylamino)-5-ethoxycarbonyl-6-ethylpyrimidine

In analogy to Example 2, 1.00 g (4.66 mmol) of 4-chloro-5-ethoxycarbonyl-6-ethylpyrimidine, 0.76 g (4.85 mmol) of cis-4-tert-butylcyclohexylamine and 0.94 g (9.29 mmol) of triethylamine gave 1.1 g (70% of theory) of the product as a colorless solid.

m.p.: 69° to 70° C.

Example 5

4-(cis-4-tert-Butylcyclohexylamino)-6-ethyl-5-methoxycarbonylpyrimidine 5.8 g (15 mmol) of 4-(cis-tert-butylcyclohexylamino)-6-ethyl-5-iodopyrimidine (Example 1) were reacted with 80 bar of carbon monoxide in an autoclave at 50° C. in the presence of 2.5 g of triethylamine and 0.1 g of bis(triphenylphosphine)palladium dichloride in 100 ml of methanol. The catalyst was removed by filtration and the filtrate was concentrated. Chromatography on silica gel (petroleum ether/ethyl acetate 7:3) gave 2.1 g (30.3% of theory) of colorless oil.

Example 6

6-Ethyl-5-methoxycarbonyl-4-(cis-4-trimethylsilylcyclohexylamino)pyrimidine 12.4 g (62.0 mmol) of 4-chloro-6-ethyl-5-methoxycarbonylpyrimidine, 11.1 g (62.0 mmol) of cis-4-trimethylsilylcyclohexylamine and 12.55 g (124 mmol) of triethylamine were heated in 30 ml of toluene at 90° C. for 3 hours. After complete reaction, the mixture was partitioned between dichloromethane and water to give, after further extraction with dichloromethane and column chromatography on silica gel, 17.76 g (85.4% of theory) of the cyclohexylaminopyrimidine as a pale brown oil, $n_D^{21}$=1.5230.

Preparation of the precursor 4-chloro-6-ethyl-5-methoxycarbonylpyrimidine 20 g (74.5 mmol) of 4-chloro-6-ethyl-5-iodopyrimidine, 12.6 g (125 mmol) of triethylamine and 0.86 g (0.7 mmol) of tetrakistriphenylphosphinepalladium(0) were reacted for 24 hours at 70° C. and 100 bar carbon monoxide pressure. The solvent was removed and the solid residue was partitioned between water and ethyl acetate. Further extraction and column chromatography gave 12 g (80% of theory) of the methoxycarbonylpyrimidine as a colorless oil, $n_D^{21}$=1.5063.

Example 7

4-(cis-4-tert-Butylcyclohexylamino)-6-ethyl-5-(trimethylsilylethynyl)pyrimidine 6.5 g (17 mmol) of 4-(cis-4-tert-butylcyclohexylamino)-6-ethyl-5-iodopyrimidine (Example 1), 3.24 g (33 mmol) of bis(triphenyl)palladium(II) chloride and 0.035 g (0.2 mmol) of copper(I) iodide were stirred in 20 ml of triethylamine at 50° C. for 6 hours. The mixture was worked up by concentrating it, taking up the residue in toluene, filtering off the insoluble material and concentrating the filtrate. Chromatography on silica gel left 4.1 g (61.6% of theory) of colorless oil.

Example 7a

4-(cis-4-tert-Butylcyclohexylamino)-5-ethynyl-6-ethylpyrimidine 2.8 g (7.7 mmol) of 4-(cis-4-tert-butylcyclohexylamino)-6-ethyl-5-(trimethylsilylethynyl)pyrimidine (Example 7) were stirred in 25 ml of a 0.4 molar solution of potassium hydroxide in methanol at room temperature for 4 hours. The mixture was concentrated, the residue was taken up in toluene/water and the organic phase was dried and concentrated to leave 1.85 g (84.2% of theory) of a colorless solid.

m.p.: 96° to 97° C.

Example 8

6-Ethyl-5-iodo-4-(cis-4-phenylcyclohexylamino)pyrimidine

Prepared as in Example 1 from 4-chloro-5-iodo-6-ethylpyrimidine and cis-4-phenylcyclohexylamine.

m.p.: 90° to 91° C.

Example 9

6-Ethyl-4-(cis-4-phenylcyclohexylamino)-5-trimethylsilylethynylpyrimidine

Prepared as in Example 7 from 6-ethyl-5-iodo-4-(cis-4-phenylcyclohexylamino)pyrimidine (Example 8) and trimethylsilylacetylene (colorless solid).

Example 10

5-Ethynyl-6-ethyl-4-(cis-4-phenylcyclohexylamino)pyrimidine

Prepared as in Example 6 from 6-ethyl-4-(cis-4-phenylcyclohexylamino)-5-trimethylsilylethynylpyrimidine (Example 9) by eliminating the silyl group in methanolic potassium hydroxide solution.

m.p.: 92° to 93° C.

Example 11

6-Ethyl-5-iodo-6-(cis-4-trimethylsilylcyclohexylamino)pyrimidine

Prepared as in Example 1 from 4-chloro-5-iodo-6-ethylpyrimidine and cis-4-trimethylsilylcyclohexylamine (yellow oil). The following compounds were further prepared analogously:

Example 11a

6-Ethyl-5-iodo-4-[cis-4-[dimethyl-(2-ethoxyethyl)silyl]-cyclohexylamino]pyrimidine, colorless oil

Example 11b

6-Ethyl-5-iodo-4-[cis-4-(dimethylmethoxymethylsilyl)-cyclohexylamino]pyrimidine, colorless oil

Examples 12 to 18 (Table 1)

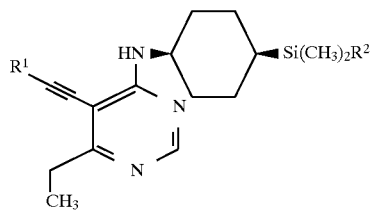

Prepared as in Example 7 from in each case 5 mmol of one of the silylcyclohexylamino derivatives of Examples 11 to 11b, 15 mmol of acetylene component, 150 mg of tetrakis(triphenylphosphine)palladium(0) and 100 mg of copper(I) iodide.

TABLE 1

| Ex. No. | $R^1$ | $R^2$ | m.p. [°C.] | Yield [%] |
|---|---|---|---|---|
| 12 | $Si(CH_3)_3$ | $CH_3$ | Resin | 78.5 |
| 13 | $Si(CH_3)_3$ | $CH_2OCH_3$ | Resin | 63.4 |
| 14 | $Si(CH_3)_3$ | $(CH_2)_2OC_2H_5$ | Resin | 72.3 |
| 15 | $Si(C_2H_5)_3$ | $CH_3$ | Resin | 71.7 |
| 16 | $Si(i-C_3H_7)$ | $CH_3$ | Resin | 70.7 |
| 17 | $Si(C_6H_5)_3$ | $CH_3$ | 95 to 97 | 69.7 |
| 18 | $CH_3$ | $CH_3$ | Resin | 44.0 |

Examples 19 to 20a

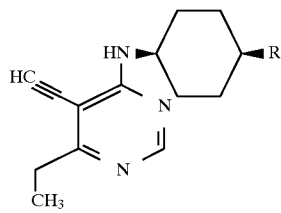

2.7 mmol of a trimethylsilyl compound from Table 1 ($R^1=Si(CH_3)_3$) were stirred at room temperature under inert gas in 0.4N methanolic KOH until the protecting group had been eliminated completely. The solvent was removed in vacuo, the solid residue was taken up in water and neutralized and the mixture was extracted with dichloromethane. Chromatography on silica gel gave the alkines as colorless oils.

TABLE 2

| Ex. No. | R | Yield [%] |
|---|---|---|
| 19 | $Si(CH_3)_3$ | 82.3 |
| 20 | $Si(CH_3)_2CH_2OCH_3$ | 72.4 |
| 20a | $Si(CH_3)_2(CH_2)_2OC_2H_5$ | 82.9 |

Example 21

5-(tert-Butyldimethylsilylethynyl)-6-ethyl-4-(cis-4-trimethylsilylcyclohexylamino)pyrimidine 1.0 g (3.3 mmol) of 5-ethynyl-6-ethyl-4-(cis-4-trimethylsilylcyclohexylamino)pyrimidine (Example 19) dissolved in 5 ml of absolute THF was added to 1.8 ml of a 3.0M solution of methylmagnesium chloride. After 1 hour, 1.25 g (8.3 mmol) of tert-butyldimethylsilyl chloride in 10 ml of absolute THF were added dropwise and the mixture was stirred at room temperature. Hydrolysis, extraction with ether and column chromatography gave 0.26 g (19% of theory) of the silylated acetylene (colorless oil) and 0.33 g (0.11 mmol)=33% of the starting material.

Example 22

4-(cis-4-tert-Butylcyclohexylamino)-6-ethyl-5-vinylpyrimidine 3.9 g (10 mmol) of 4-(cis-4-tert-butylcyclohexylamino)-6-ethyl-5-iodopyrimidine (Example 1) were treated with 10 bar of ethylene in an autoclave at 120° C. in the presence of 1.5 g (15 mmol) of potassium acetate and 50 mg of palladium black in 100 ml of methanol. After 24 hours, the catalyst was removed by filtration and the mixture was concentrated. Chromatography on silica gel gave 1.70 g (61.8% of theory) of colorless oil.

Example 23

5-Cyanoethyl-6-(cis-4-phenylcyclohexylamino)pyrimidine

Prepared as in Example 2 from 6-ethyl-5-iodo-4-(cis-4-phenylcyclohexylamino)pyrimidine (Example 8) and copper(I) cyanide, colorless solid, m.p. 58°–59° C.

Example 24

6-Ethyl-4-(cis-4-phenylcyclohexylamino)-5-vinylpyrimidine

Starting from 4.07 g (10 mmol) of 6-ethyl-5-iodo-6-(4-phenylcyclohexylamino)pyrimidine (Example 8) and in analogy to Example 22, 1.94 g (63.2% of theory) of yellow solid were obtained.

m.p.: 53° to 54° C.

Example 25

4-(cis-4-tert-Butylcyclohexylamino)-5-chloro-6-vinylpyrimidine

A solution of 7.6 g (21 mmol) of 4-(cis-4-tert-butylcyclohexylamino)-5-chloro-6-(1-methylsulfinylethyl)pyrimidine (Example 26) in 100 ml of diethylene glycol dimethyl ether to which a little hydroquinone had been added was heated at 150° C. for 30 minutes. After cooling to room temperature the mixture was poured into water and extracted by stirring with dichloromethane. This left a brown oil which was extracted twice by stirring with petroleum ether. The petroleum ether phase was concentrated and the residue was purified with chromatography on silica gel, to give 1.1 g (17.8% of theory) of colorless solid.

m.p.: 51°–52° C.

Example 26

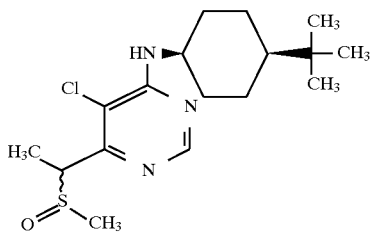

4-(cis-4-tert-Butylcyclohexylamino)-5-chloro-6-(1-methylsulfinylethyl)pyrimidine 10.25 g (30 mmol) of 4-(cis-4-tert-butylcyclohexylamino)-5-chloro-6-(1-methylthioethyl)pyrimidine were placed in 120 ml of dichloroethane, and a solution of 7.40 g (30 mmol) of 70% 3-chloroperbenzoic acid in 50 ml of dichloromethane was added dropwise at 0° C. The mixture was stirred at room temperature for 8 hours and extracted by stirring with sodium bicarbonate solution and water. The organic phase was dried and concentrated, to give 10.5 g (98% of theory) of a colorless resin (diastereomer mixture).
Preparation of the precursor 4-(cis-4-tert-butylcyclohexylamino)-5-chloro-6-(1-methylthioethyl)pyrimidine 19.8 g (60 mmol) of 4-(cis-4-tert-butylcyclohexylamino)-5-chloro-6-(1-chloroethyl)pyrimidine and 4.2 g (60 mmol) of sodium methanethiolate were heated at reflux in 100 ml of methanol for 6 hours. The mixture was concentrated and the residue was taken up in water/toluene. The organic phase was dried and concentrated, to give 17.7 g (85% of theory) of a colorless resin which was subsequently reacted without further purification.
Preparation of the precursor 4-(cis-4-tert-butylcyclohexylamino)-5-chloro-6-(1-chloroethyl)pyrimidine 32.3 g (0.15 mol) of 4,5-dichloro-6-(1-chloroethyl)pyrimidine(EP 543 402) were stirred in 200 ml of toluene with 23.3 g (0.15 mol) of cis-4-tert-butylcyclohexylamine and 20.2 g (0.20 mol) of triethylamine at from 80° to 90° C. for 6 hours. The mixture was extracted by stirring with water and the organic phase was dried and concentrated. The residue was purified by chromatography on silica gel, to give 36.3 g (73.2% of theory) of a colorless oil.

Example 27

4-(cis-4-tert-Butylcyclohexylamino)-5-chloro-6-(trimethylsilylethynyl)pyrimidine In analogy to Example 7, 1.6 g (4 mmol) of 4-(cis-4-tert-butylcyclohexylamino)-5-chloro-6-iodopyrimidine, 2.0 g of trimethylsilylacetylene, 100 mg of bis-triphenylphosphine palladium dichloride and 20 mg of copper(I) iodide in 20 ml of triethylamine gave, after chromatography on silica gel (petroleum ether/ethyl acetate 9:1), 0.7 g (47.3% of theory) of a colorless oil which gradually crystallized.

m.p.: 92° to 93° C.
Preparation of the precursor 4-(cis-4-tert-butylcyclohexylamino)-5-chloro-6-iodopyrimidine 3.6 g (10 mmol) of 4-(cis-4-tert-butylcyclohexylamino)-6-iodopyrimidine and 2.0 g of N-chlorosuccinimide were heated at reflux for 8 hours in 15 ml of chloroform. After cooling to room temperature, the mixture was extracted by stirring with dilute sodium hydroxide solution and water and the organic phase was dried and concentrated. The residue was purified by chromatography on silica gel (petroleum ether/ethyl acetate 4:1) to give first of all 2.3 g (58.4% of theory) of product (a colorless oil which gradually crystallized, m.p. 89° to 90° C.) and, finally, 1.0 g of unreacted starting material.

Preparation of the precursor 4-(cis-4-tert-butylcyclohexylamino)-6-iodopyrimidine 2.0 g (7.5 mmol) of 4-(cis-4-tert-butylcyclohexylamino)-6-chloropyrimidine were heated at reflux for 5 hours in 20 ml of aqueous hydroiodic acid (57% strength). After cooling the mixture was filtered with suction, the solid was suspended in water and the suspension was rendered basic using ammonia solution. It was extracted with dichloromethane and the organic phase was dried and concentrated, to leave 1.2 g (44.5% of theory) of colorless resin which gradually crystallized.

m.p.: 99° to 100° C.

Preparation of the precursor 4-(cis-4-tert-butylcyclohexylamino)-6-chloropyrimidine 58.6 g (0.39 mol) of 4,6-dichloropyrimidine were placed in 400 ml of toluene, and a mixture of 61.0 g (0.39 mol) of cis-4-tert-butylcyclohexylamine and 50.0 g (0.50 mol) of triethylamine in 100 ml of toluene was added dropwise at from 70° to 80° C. The mixture was subsequently stirred at reflux for 4 hours. After cooling, it was extracted by stirring with water, the organic phase was dried and concentrated, to give a colorless oil which crystallized after trituration with petroleum ether. Filtration with suction left 70.5 g (67.0% of theory) of colorless crystals.

m.p.: 112° to 113° C.

Example 28

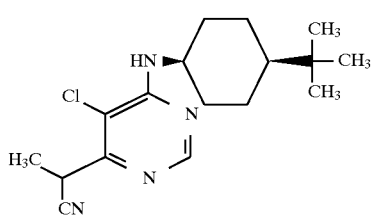

4-(cis-4-tert-Butylcyclohexylamino)-5-chloro-6-(1-cyanoethyl)pyrimidine 3.3 g (10 mmol) of 4-(cis-4-tert-butylcyclohexylamino)-5-chloro-6-(1-chloroethyl)pyrimidine (precursor to Example 26) and 1.3 g (20 mmol) of potassium cyanide were heated at reflux in 20 ml of ethanol in the presence of 250 mg of potassium iodide. After stripping off the solvent, the residue was taken up in water/toluene and the organic phase was dried and concentrated. Chromatography on silica gel (petroleum ether/ethyl acetate 7:3) gave, after 1.0 g of starting material, 1.1 g (34.3% of theory) of product as colorless oil.

Example 29

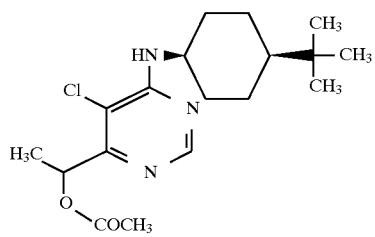

6-(1-Acetoxyethyl)-4-(cis-tert-butylcyclohexylamino)-5-chloropyrimidine 10.0 g (42.5 mmol) of 6-(1-acetoxyethyl)-4,5-dichloropyrimidine (EP 543 402), 6,6 g (42.5 mmol) of cis-4-tert-butylcyclohexylamine and 4.7 g (46.9 mmol) of triethylamine were stirred in 100 ml of toluene at from 80° to 90° C. for 6 hours. The mixture was extracted by stirring with water and the organic phase was dried and concentrated, to leave 15.0 g (100% of theory) of a colorless oil.

Example 30

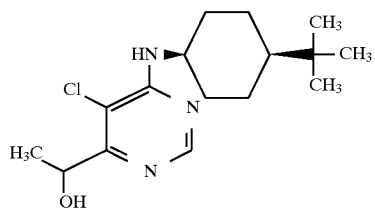

4-(cis-4-tert-Butylcyclohexylamino)-5-chloro-6-(1-hydroxyethyl)pyrimidine 1.5 g (40 mmol) of lithium aluminum hydride were placed in 100 ml of dry tetrahydrofuran, and a solution of 14 g (40 mmol) of 6-(1-acetoxyethyl)-4-(cis-4-tert-butylcyclohexylamino)-5-chloropyrimidine (Example 30) in 50 ml of dry tetrahydrofuran was added dropwise at a temperature of 20° to 30° C. The mixture was then heated at reflux for 2 hours. After cooling, 5 ml of water were added carefully dropwise and, after standing overnight, the mixture was filtered with suction to remove the inorganic material. The filtrate was concentrated and the residue was chromatographed on silica gel (ethyl acetate/methanol 9:1) to give 6.0 g (48.1% of theory) of a colorless oil.

Example 31

Ethyl [4-(cis-4-tert-butylcyclohexylamino)-6-methylpyrimidin-5-yl]acetate 15.2 g (71 mmol) of methyl (4-chloro-6-methylpyrimidin-5-yl)acetate, 11.0 g (71 mmol) of cis-4-tert-butylcyclohexylamine and 20.2 g (0.2 mol) of triethylamine were heated at 80° to 90° C. for 6 hours without solvent. After cooling, the mixture was taken up in water/toluene and the organic phase was dried and concentrated. In the chromatography on silica gel (petroleum ether/ethyl acetate 1:1, then ethyl acetate/methanol 9:1), 5.3 g of chloropyrimidine starting material were first of all retained and then 10.0 g (27.7% of theory) of product were obtained as a yellow solid.

m.p.: 68° to 69° C.

Preparation of the precursor ethyl (4-chloro-6-methylpyrimidin-5-yl)acetate 30.6 g (0.16 mol) of ethyl (4-hydroxy-6-methylpyrimidin-5-yl)acetate, 17.8 g (0.18 mol) of triethylamine and 263.2 g (1.72 mol) of phosphorus oxychloride were heated at reflux for 4 hours. The excess phosphorus oxychloride was stripped off, the residue was taken up in dichloromethane, and the mixture was added dropwise to 500 ml of sodium bicarbonate solution and neutralized by addition of solid sodium bicarbonate. The organic phase was separated off, dried and concentrated to give 30.4 g (88.5% of theory) of a dark oil which was reacted further without purification.

Preparation of the precursor ethyl (4-hydroxy-6-methylpyrimidin-5-yl)acetate 216.24 g (1.0 mol) of ethyl acetylsuccinate and 104.11 g (1.0 mol) of formamidine acetate were placed in 500 ml of ethanol, and 360.13 g (2.0 mol) of 30% methanolic sodium methylate solution were added dropwise at 0° C. The mixture was stirred at room temperature for 6 hours and concentrated and the residue was taken up in toluene/water. The aqueous phase was brought to a pH of 3–4 with conc. hydrochloric acid and extracted by stirring a number of times with dichloromethane. Drying and concentration of the combined dichloromethane phases left a resinous solid. This solid was stirred with a mixture of diisopropyl ether and ethyl acetate (2:1) which was then filtered with suction to leave 55.6 g (28.3% of theory) of colorless crystals of m.p. 148° to 149° C.

Example 32

Ethyl [6-Methyl-4-(cis-4-phenylcyclohexylamino) pyrimidin-5-yl]acetate

In analogy to Example 31, 15.2 g (0.071 mol) of ethyl [4-chloro-6-methylpyrimidin-5-yl]acetate (precursor to Example 31), 12.4 g (0.071 mol) of cis-4-phenylcyclohexylamine and 20.2 g (0.02 mol) of triethylamine gave, in addition to 7.5 g of recovered chloropyrimidine, 5.0 g (19.9% of theory) of product as a dark resin.

Example 33

4-(cis-4-tert-Butylcyclohexylamine)-5-(2-hydroxyethyl)-6-methyl-pyrimidine

A solution of 8.26 g (25 mmol) of ethyl [4-(cis-4-tert-butyl-cyclohexylamino)-6-methylpyrimidin-5-yl]acetate (Example 31) in 50 ml of dry tetrahydrofuran was added dropwise to a suspension of 1.14 g (30 mmol) of lithium aluminum hydride in 100 ml of dry tetrahydrofuran. The mixture was stirred at 50° C. for 2 hours, cooled and decomposed by the dropwise addition of 20 ml of ethyl acetate and 10 ml of water. After standing overnight it was filtered with suction and the filtrate was dried and concentrated. Chromatography of the crude product on silica gel (ethyl acetate/methanol 4:1) left 4.31 g of a yellow solid.

m.p.: 150° to 152° C.

Example 34

5-(2-Hydroxyethyl)-6-methyl-4-(cis-4-phenylcyclohexylamino)pyrimidine

In analogy to Example 33, 4.0 g (11 mol) of ethyl [6-methyl-4-(cis-4-phenylcyclohexylamino)pyrimidin-5-yl] acetate (Example 32) and 0.46 g (12 mmol) of lithium aluminum hydride gave 1.83 g (53.4% of theory) of product.

m.p. 134° to 136° C.

Example 35

4-(cis-4-tert-Butylcyclohexylamino)-6-methyl-5-(2-fluoroethyl)pyrimidine 2.0 g (6.5 mmol) of 4-(cis-4-tert-butylcyclohexylamino)-6-methyl-5-(2-hydroxyethyl)pyrimidine (Example 33) were dissolved in 30 ml of dichloromethane, and 1.16 g (7.2 mmol) of diethylaminosulfur trifluoride (DAST) were added at −50° C. The mixture was allowed to rise to room temperature, and was subsequently stirred for 4 hours. It was poured into water, the dichloromethane phase was extracted by stirring with sodium hydrogen carbonate solution and the organic extracts were dried and concentrated. Chromatography on silica gel gave 1.55 g (77.6% of theory) of product as colorless oil.

Example 36

5-(2-Fluoroethyl)-6-methyl-4-(cis-4-phenylcyclohexylamino)pyrimidine

In analogy to Example 35, 1.13 g (3.6 mmol) of 5-(2-hydroxyethyl)-6-methyl-4-(cis-4-phenylcyclohexylamino) pyrimidine (Example 34) and 0.66 g (41 mmol) of DAST gave, after chromatography on silica gel, 0.76 g (67.4% of theory) of product as a colorless oil.

Example 37

6-Ethyl-5-hydroxymethyl-4-(cis-4-trimethylsilylcyclohexylamino)pyrimidine

A solution of 7.0 g (20.9 mmol) of 5-methoxycarbonyl-6-ethyl-4-(cis-4-(trimethylsilyl)cyclohexylamino) pyrimidine (Example 6) in 30 ml of absolute tetrahydrofuran was added dropwise to a suspension, cooled to −30° C., of 1.03 g (27.1 mmol) of lithium aluminum hydride in 10 ml of absolute tetrahydrofuran, and the mixture was stirred at room temperature until the end of reaction. Following the hydrolysis, the mixture was subjected to extraction with diethyl ether to give, after drying and removal of the solvent, 6.13 g (19.9 mmol)=95% of the hydroxymethyl compound in the form of white crystals.

m.p.=136° to 138° C.

Example 38

Ethyl [4-(cis-4-tert-butylcyclohexylamino) pyrimidin-6-yl]acetate 1.80 g (9 mmol) of ethyl (4-chloropyrimidin-6-yl)acetate, 1.40 g (9 mmol) of cis-4-tert-butylcyclohexylamine and 1.82 g (18 mmol) of triethylamine were heated at 80° to 90° C. for 8 hours. After cooling, the mixture was taken up in water/toluene and the organic phase was dried and concentrated. Purification was carried out by chromatography on silica gel (ethyl acetate) to give 1.85 g (64.4% of theory) of a colorless resin.

Preparation of the precursor ethyl (4-chloropyrimidin-6-yl) acetate 2.7 g (50 mmol) of sodium hydride (80% dispersion in oil) were placed in 100 ml of dry dioxane, and 11.7 g (90 mmol) of ethyl acetoacetate were added dropwise. The mixture was then stirred at 50° C. for 1 hour. After cooling to room temperature, a solution of 4.5 g (30 mmol) of 4,6-dichloropyrimidine in 50 ml of dioxane was added dropwise. After heating at reflux for 6 hours the mixture was cooled to room temperature, 10 ml of methanol were added dropwise in order to destroy superfluous sodium hydride, and the mixture was concentrated. The residue was taken up in water and brought to a pH of 3 to 4 with conc. hydrochloric acid. After extractive stirring with toluene, the organic phase was dried and concentrated. Chromatography on silica gel left 1.8 g (30% of theory) of a colorless oil.

Example 39

4-(cis-4-tert-Butylcyclohexylamino)-5-chloro-6-ethynylpyrimidine 0.64 g (1.76 mmol) of 4-(cis-4-tert-butylcyclohexylamino)-5-chloro-6-trimethylsilylethynylpyrimidine (Example 27) was dissolved in 20 ml of tetrahydrofuran, and 2 ml of a 1.0M solution of tetrabutylammonium fluoride in tetrahyrofuran were added at 0° C. The mixture was stirred at room temperature for 2 hours, diluted with toluene and exracted by stirring with sodium hydrogen carbonate solution and water. The organic phase was dried and concentrated. Chromatography on silica gel left 0.44 g (86.0% of theory) of a colorless oil which gradually solidified.

m.p.: 124° to 125° C.

Example 40

4-(cis-4-tert-Butylcyclohexylamino)-6-carbomethoxy-5-chloropyrimidine

This compound was obtained in analogy to Example 5, from 4-(cis-4-tert-butylcyclohexylamino)-5-chloro-6-iodopyrimidine (precursor for Example 27), in 55% yield as a colorless oil.

Example 41

4-(cis-4-tert-Butylcyclohexylamino)-5-chloro-6-cyanopyrimidine

In analogy to Example 2, 3.9 g (10 mmol) of 4-(cis-4-tert-butylcyclohexylamino)-5-chloro-6-iodopyrimidine and 1.8 g (20 mmol) of copper(I) cyanide gave, after chromatography on silica gel (petroleum ether/ethyl acetate 9:1), 0.9 g (30.8% of theory) of product as a colorless oil which gradually solidified.

m.p.: 107° to 108° C.

Example 42

4-(cis-4-tert-Butylcyclohexylamino)-6-ethyl-5-fluoromethylpyrimidine

This compound can be prepared starting from 5-carbomethoxy-4-(cis-4-tert-butylcyclohexylamino)-6-ethylpyrimidine (Example 5) by reduction to the 5-hydroxymethyl compound (in analogy to Example 37) and fluorination with diethylaminosulfur trifluoride (DAST).

EXAMPLES FOR PREPARATION PROCESS 2

Example 43

4-(cis-4-tert-Butylcyclohexylamino )-6-ethyl-5-trifluoromethylpyrimidine 8.4 g of trifluoromethyl iodide and 5 g of copper powder were stirred with 20 ml of hexamethylphosphoric triamide in a stainless steel laboratory autoclave (Hastelloy) at 120° C. for 2.5 hours. The mixture was filtered with suction over Celite, under nitrogen, to remove the excess copper powder. 1.92 g (5 mmol) of 4-(cis-4-tert-butyl-cyclohexylamino)-6-ethyl-5-iodopyrimidine (Example 1) were added in order to dissolve the trifluoromethyl-copper complex, and the mixture was stirred under nitrogen at 100° C. for 2 hours. After cooling, 200 ml of diethyl ether were added, the precipitated copper salts were filtered off and the filtrate was extracted by stirring with water. The organic phase was dried and concentrated. The product was purified by filtration over a silica gel column (petroleum ether/ethyl acetate 7:3) to give 0.52 g (32% of theory) of product as a colorless oil.

Example 43a 4-(cis-4-tert-Butylcyclohexylamino)-6-ethyl-5-pentafluoroethylpyrimidine Prepared as in Example 43 from pentafluoroethyl iodide and 4-(cis-4-tert-butylcyclohexylamino)-6-ethyl-5-iodopyrimidine (Example 1), colorless oil.

Example 44

4-(cis-4-tert-Butylcyclohexylamino)-6-ethyl-5-trifluoromethylthiopyrimidine 1.93 g (5 mmol) of 4-(cis-4-tert-butylcyclohexylamino)-6-ethyl-5-iodopyrimidine (Example 1) and 1.64 g (10 mmol) of trifluoromethylthio copper (Synthesis 1975, 721) were stirred in 20 ml of dimethylformamide, under nitrogen, at 150° C. for 7 hours. After cooling, the mixture was diluted with 200 ml of water and subjected to extraction by stirring with ether. The organic phase was again washed with water, dried and concentrated. The crude product was purified by filtration over a silica gel column (petroleum ether/ethyl acetate 7:3), to give 0.59 g (33% of theory) of product as a colorless oil.

Example 45

6-Ethyl-5-methoxy-4-(cis-4-phenylcyclohexylamino)pyrimidine 7.20 g (20 mmol) of 5-bromo-6-ethyl-4-(cis-4-phenylcyclohexylamino)pyrimidine (DE-A-42 08 254) and 0.44 g (3 mmol) of copper(I) bromide were heated under reflux for 12 hours in 10 ml of 30% methanolic sodium methylate solution, to which 0.70 g of ethyl acetate have been added. For working up, the solvent is stripped off, the residue is taken up in ethyl acetate, this mixture is subjected to extraction by stirring with water, and the organic phase is dried and concentrated. For purification, the crude product is chromatographed on silica gel using ethyl acetate/petroleum ether (8:2). 3.7 g (60% of theory) of a colorless oil were obtained which gradually solidified.

m.p.: 79° to 80° C.

Example 46

4-(cis-4-tert-Butylcyclohexylamino)-6-ethyl-5-methoxypyrimidine

In analogy to Example 7, 6.8 g (20 mmol) of 5-bromo-4-(cis-4-tert-butylcyclohexylamino)-6-ethylpyrimidine and 10 ml of 30% methanolic sodium methylate solution gave, with addition of 0.44 g of copper(I) bromide and 0.70 g of ethyl acetate, 1.9 g (33% of theory) of product as a colorless oil.

The following compounds were also obtained in analogy to Example 44:

Example 47

4-(cis-4-tert-Butylcyclohexylamino)-5-ethoxy-6-ethylpyrimidine, colorless oil.

Example 48

6-Ethyl-5-methoxy-4-[cis-4-(1,1,3,3-tetramethylbutyl)-cyclohexylamino]pyrimidine, colorless oil.

Example 49

6-Ethyl-5-methoxy-4-(cis-4-trimethylsilylcyclohexylamino)pyrimidine, colorless oil.

Example 50

6-Ethyl-4-(2-decylamino)-5-methoxypyrimidine, colorless oil.

Example 51

6-Ethyl-4-[2-(2,4-dimethylphenoxy)ethylamino]-5-methoxypyrimidine

Example 52

6-Ethyl-5-isopropoxy-4-(cis-4-tert-butylcyclohexylamino)pyrimidine, colorless oil.

Example 53

5-Ethoxy-6-ethyl-4-(cis-4-phenylcyclohexylaminopyrimidine, colorless oil.

Example 54 to 61

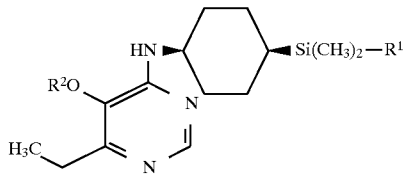

TABLE 3

| Ex. No. | $R^1$ | $R^2$ |
|---|---|---|
| 54 | —(CH$_2$)$_3$O(CH$_2$)$_2$OC$_2$H$_5$ | CH$_3$ |
| 55 | —(CH$_2$)$_3$(OCH$_2$CH$_2$)O$_2$C$_2$H$_5$ | CH$_3$ |
| 56 | —(CH$_2$)$_2$OC$_2$H$_5$ | CH$_3$ |
| 57 | —(CH$_2$)$_2$OC$_2$H$_5$ | C$_2$H$_5$ |
| 58 | (CH$_2$)$_3$O(CH$_2$)$_2$OCH(CH$_3$)$_2$ | CH$_3$ |
| 59 | (CH$_2$)$_2$Si(CH$_3$)$_3$ | CH$_3$ |
| 60 | (CH$_2$)$_3$Si(CH$_3$)$_3$ | CH$_3$ |
| 61 | (CH$_2$)$_2$CH(CH$_3$)$_3$ | CH$_3$ |

All of the examples from Table 3 were isolated as colorless oils.

In analogy to the examples given above, it is also possible to prepare derivatives with different side chains X-E-Q from formula 1, for example with the radicals:

cis-4-n-propylcyclohexylamino,
cis-4-isopropylcyclohexylamino,
cis-4-n-butylcyclohexylamino,
cis-4-sec-butylcyclohexylamino,
cis-4-isobutylcyclohexylamino,
cis-4-(tert-amylcyclohexylamino,
cis-4-n-hexylcyclohexylamino,
cis-4-n-octylcyclohexylamino,
cis-4-(1,1,3,3-tetramethylbutyl)cyclohexylamino,
cis-4-(1,1,3,3-tetramethylbutyl)cyclohexyloxy,
cis-4-cyclopentylcyclohexylamino,
cis-4-(1-methylcyclopentyl)cyclohexylamino,
cis-4-cyclohexylcyclohexylamino,
cis-4-(1-methylcyclohexyl)cyclohexylamino,
cis-4-trimethylsilylcyclohexylamino,
cis-4-trifluoromethylcyclohexylamino,
cis-4-phenylcyclohexylamino,
cis-4-(4-methylphenyl)cyclohexylamino,
cis-4-(4-ethylphenyl)cyclohexylamino,
cis-4-(4-tert-butylphenyl)cyclohexylamino,
cis-4-(4-trifluoromethylphenyl)cyclohexylamino,
cis-4-(4-trimethylsilylphenyl)cyclohexylamino,
cis-4-(4-ethynylphenyl)cyclohexylamino,
cis-4-(4-chlorophenyl)cyclohexylamino,
cis-4-(4-fluorophenyl)cyclohexylamino,
cis-4-(4-methoxyphenyl)cyclohexylamino,
cis-4-(4-ethoxyphenyl)cyclohexylamino,
cis-4-(4-isopropoxyphenyl)cyclohexylamino,
cis-4-(4-trifluoromethoxyphenyl)cyclohexylamino,
cis-4-vinylcyclohexylamino,
cis-4-phenylcyclohexyloxy,
cis-4-benzylcyclohexylamino,
cis-4-ethoxycyclohexylamino,
cis-4-n-propoxycyclohexylamino,
cis-4-isopropoxycyclohexylamino,
cis-4-n-butoxycyclohexylamino,
cis-4-cyclohexyloxycyclohexylamino,
cis-4-phenoxycyclohexylamino,
cis-4-(4-methylphenoxy)cyclohexylamino,
4-tert-butylcycloheptylamino,
4-phenylcycloheptylamino,
3-ethylcyclopentylamino,
3-tert-butylcyclopentylamino,
3-tert-amylcyclopentylamino,
3-phenylcyclopentylamino,
3-tert-butylcyclobutylamino,
3-phenylcyclobutylamino,
(4-tert-butylcyclohex-1-yl)methylamino,
(4-phenylcyclohex-1-yl)methylamino,
4-tert-butoximinocyclohexylamino.

C. BIOLOGICAL EXAMPLES

Insecticidal Action

Example 1: Action on the Rice Brown Planthopper

Young rice plants (*Oryza sativa*) were dipped into aqueous dilutions of a wettable powder concentrate having a concentration of 250 ppm (based on active substance) and, after the drops had run off, these plants were populated with L4 larvae of the rice brown planthopper *Nilaparvata lugens*.

After placing the treated plants in an experimental cage, they were observed for 3 days at 28° C. and high atmospheric humidity, and the mortality of the test organisms was determined.

At 250 ppm, the compounds according to Example 2, 2a, 5, 7, 7a, 8, 10, 11, 11a, 12, 14, 18, 19, 20a, 22, 25, 29, 30, 43, 43a, 44, 45, 46, 49, 50, 51, 55, 56, 59, 60 and 61 produced 100% mortality in the test organisms.

Example 2: Action on Diabrotica Undecimpunctata

Larvae (L2) of the southern corn rootworm (*Diabrotica undecimpunctata*) were placed on filter paper disks which had each been soaked with 1 ml of an acetone-diluted formulation of a wettable powder in a concentration of 250 ppm based on active substance. After the acetone had evaporated, the dishes were sealed and stored at 28° C. for 3 days, after which the mortality of the larvae was determined.

100% mortality was found with the compounds according to Example 1, 2, 2a, 7, 7a, 8, 10, 11, 11a, 12, 13, 14, 18, 19, 20a, 22, 24, 25, 29, 30, 43, 43a, 44, 45, 46, 47, 49, 50, 53, 54, 55, 56, 57, 58, 59, 60 and 61.

Example 3: Action on the Black Bean Aphid

Field bean plants (*Vicia faba*) which were severely infested with black bean aphids (*Aphis fabae,* full population) were sprayed to the beginning of runoff with an aqueous preparation comprising 250 ppm of the active substance in question. After the plants had been grown in the greenhouse for 3 days, the mortality of the aphids (full population) was checked. 100% mortality was found in the case of Examples 1, 2, 2a, 3, 5, 7, 7a, 8, 10, 11, 11a, 11b, 12, 13, 14, 18, 19, 20a, 22, 24, 25, 43, 45, 49, 50, 51, 53, 54, 55, 56, 57, 58, 59, 60 and 61.

Example 4: Action on the Common Citrus Mealy Bug

Bean plants (*Phaseolus vulgaris ssp. vulgaris var. nanus*) which were severely infested with common citrus mealy bugs (*Planococcus citri,* 2nd instar larvae) were sprayed to the beginning of runoff with an aqueous preparation comprising 250 ppm of the active substance in question. After the plants had been grown in the greenhouse for 7 days, the mortality of the common citrus mealy bug (full population) was checked. 100% mortality was found in the case of Example 2.

Example 5: Action on the Common Housefly

The bottom and lid of a Petri dish were coated on the inside with in each case 3 ml of an aqueous dilution of a wettable powder concentrate comprising 250 ppm of the active substance in question. After the coating had dried on, 24-hour-old common houseflies (*Musca domestica*) were placed in the Petri dishes, which were sealed with the treated lid. After 3 hours at 20° C., the mortality of the flies was checked. 100% mortality was obtained with the compounds 1, 2, 2a, 7a, 8, 11, 11a, 11b, 12, 18, 19, 20a, 22, 28, 43, 44, 45, 46, 47, 48, 49, 50, 51, 53, 54, 56 and 61.

Example 6: Larvae (L4) of the Cockroach, Blaberus Craniifer, were injected with Active Substances dissolved in Methanol Following application of the compounds according to Example 1, 2, 5, 7, 7a, 8, 9, 22, 44, 45, 46, 48, 50, 51 and 53 ($2 \times 10^{-4}$ g a.i./animal), 100% mortality was found after 48 hours.

Example 7

Larvae (L4) of the tobacco hornworm, *Manduca sexta,* were injected with active substances dissolved in acetone.

Following application of the compound according to Example 1, 2, 5, 7, 7a, 8, 9, 22, 44, 45, 46, 48, 50, 51 and 53 ($2 \times 10^{-4}$ g a.i./animal), 100% mortality was found after 48 hours.

Ovicidal action

Example 8: *Manduca Sexta*

Japan filter paper was used to line the inside of the bottom of Petri dishes, and in each case 20 1-day-old eggs of *Manduca sexta* were placed on the paper. Approximately 1 ml of an artificial insect feed diet was then placed in the center of the Petri dish, and the inside of the base, together with eggs and feed diet, was sprayed with an aqueous wettable powder suspension of the test products, corresponding to 600 I/ha. After the Petri dishes had been sealed and stored at room temperature for 5 days, the mortality of the eggs was determined. 100% action was provided by the compounds of Examples 11, 11b, 12, 19, 22, 45, 46, 49, 50, 51 and 54.

Example 9: Action on the Eggs of the Large Milkweed Bug

Filter paper disks supporting eggs (egg age: 2 days) of the large milkweed bug (*Oncopeltus fasciatus*) were treated with in each case 1 ml of an aqueous preparation comprising 250 ppm of the active substance in question. After the coating had dried on, the filterpaper disks were stored in Petri dishes at room temperature and maximum atmospheric humidity. After 7 days the ovicidal action was determined. 100% ovicidal action (egg mortality) was found in the case of Examples 8, 11, 11b, 12, 19, 22, 45, 46, 49, 50, 51 and 53.

Acaricidal action

Example 10: Action on the Greenhouse Red Spider Mite

Bean plants (*Phaseolus vulgaris ssp. vulgaris var. nanus*) which were severely infected with greenhouse red spider mites (*Tetranychus urticae,* full population) were sprayed to the beginning of runoff with an aqueous preparation comprising 250 ppm of the active substance in question. After the plants had been grown in the greenhouse for 7 days, the mortality of the spider mites (full population) was checked. 100% mortality was found in the case of Example 1, 2, 2a, 3, 7a, 8, 10, 11, 11a, 11b, 12, 13, 14, 19, 20a, 22, 24, 29, 45, 46, 47, 48, 49, 50, 51, 54, 55, 56, 57, 58, 59, 60 and 61.

Example 11: Action on the Fruit Tree Red Spider Mite

Apple plants (*Malus domestics*) which were severely infested with fruit tree red spider mites (*Panonychus ulmi,* full population) were sprayed to the beginning of runoff with an aqueous preparation comprising 250 ppm of the active substance in question. After the plants had been grown in the greenhouse for 9 days, the mortality of the fruit tree red spider mites (full population) was checked. 100% mortality was found in the case of Examples 1, 2, 11, 11a, 19, 20a, 45, 46, 48, 49, 54, 55, 56, 57, 58, 59 and 60.

Nematicidal action

Example 12: Control of Root-knot Nematodes

An aqueous preparation comprising 30 ppm of active substance is prepared in a glass vessel (final volume 30 ml). To this mixture are added about 5000 freshly hatched, active (mobile) larvae (2nd instar) of root-knot nematodes (*Meloidogyne incognita*). After 48-hour exposure of the nematode larvae to the active substance, the percentage of individuals which have become motionless (immobile) by the action of said substance is determined in comparison with the untreated controls.

The compounds of Examples 2, 7, 7a, 9, 10, 12, 13, 19, 22, 25, 45, 49 and 53 showed an action of from 90 to 100% relative to the root-knot nematodes *Meloidogyne incognita.*

Use as an antiparasitic agent

Example 13

In Vitro Test on Tropical Cattle Ticks (*Boophilus microplus*)

The following experimental setup was used to demonstrate the activity of the compounds according to the invention against ticks: To prepare an appropriate preparation of active substance, the active substances were dissolved in a mixture consisting of dimethylformamide (85 g), nonylphenol polyglycol ether (3 g) and ethoxylated castor oil (7 g) to give a 10% (w/v) mixture, and the resulting emulsion concentrates were diluted with water to a test concentration of 500 ppm.

Batches of ten females of the tropical tick *Boophilus microplus* which had sucked themselves full were immersed for five minutes in these active substance dilutions. The ticks were subsequently dried on filter paper and then attached by their backs to an adhesive film in order to lay eggs. The ticks were kept in an incubator at 28° C. and an atmospheric humidity of 90%.

For control purposes, female ticks were immersed in plain water. The activity was assessed two weeks after the treatment, on the basis of inhibition of oviposition.

In this test, oviposition was inhibited to an extent of 100% by the compounds according to Examples 1, 2, 5, 7, 7a, 8, 11, 11a, 11b, 12, 13, 18, 19, 20a, 22, 45, 46, 47, 49, 51, 53, 54, 55 and 56 at an active substance concentration of 500 ppm.

Use as fungicide

The activity of the preparations according to the invention was assessed in accordance with a scale of 0–4, where 0=0–24% disease suppression 1=25–49% disease suppression 2=50–74% disease suppression 3=75–97% disease suppression 4=97–100% disease suppression.

Example 14

Barley plants of the variety "Maris Otter" at the 2-leaf stage were sprayed until dripping wet with a solution of the compounds according to the invention in a mixture of 40% acetone and 60% water. 24 hours later, the plants were inoculated with conidia of barley mildew (*Erysiphe graminis f. sp. hordei*) and stored in a controlled-environment cabinet at 20° C. and a relative atmospheric humidity of 75–80%. 7 days after the treatment, the plants were investigated for infestation with barley mildew.

The following compounds were given a rating of 3 or 4 at 500 mg of active substance/l of spray liquor: Compounds according to Example Nos. 20a, 45, 48 and 60.

Example 15

Tomato plants of the variety "First in the Field" at the 3–4-leaf stage were sprayed until dripping wet with a solution of the compounds according to the invention in a mixture of 40% acetone and 60% water. 24 hours later, the plants were inoculated with a spore suspension of *Phytophthora infestans* (20,000 spores/ml) and were stored in a controlled-environment cabinet at 15° C. first for 2 days at 99% relative atmospheric humidity and then for 4 days at 75–80% relative atmospheric humidity. 6 days after the treatment, the plants were investigated for infestation with *Phytophthora infestans*. The following compounds were given a rating of 3 or 4 at 500 mg of active substance/l of spray liquor: Compounds according to Example Nos. 43a, 46, and 47.

Example 16

Seedlings of the vine variety "Grüner Veltliner" aged about 6 weeks were sprayed until dripping wet with a solution of the compounds according to the invention in a mixture of 40% acetone and 60% water. 24 hours later the plants were inoculated by spraying with a zoospore suspension (100,000/ml) of *Plasmopara viticola* and stored in a controlled-environment cabinet at 70° C. and a relative atmospheric humidity of about 99%. 14 days after treatment the plants were investigated for their infestation with *Plasmopara viticola*. The following compounds were given a rating of 3 or 4 at 500 mg of active substance/l of spray liquor: Compounds according to Example Nos. 2, 44, 45, 47, 48, 52 and 53.

Example 17

Wheat plants of the variety "Hornet" at the 2-leaf stage were sprayed until dripping wet with a solution of the compounds according to the invention in a mixture of 40% acetone and 60% water. 24 hours later, the plants were inoculated by spraying with a pycnospore suspension (500,000/ml) of *Leptosphaeria nodorum* and stored in a controlled-environment cabinet at 18°–20° C. and a relative atmospheric humidity of about 99%. 14 days after inoculation the plants were investigated for their infestation with *Leptosphaeria nodorum*. The following compounds were given a rating of 3 or 4 at 500 mg of active substance/l of spray liquor: Compounds according to Example Nos. 3 and 49.

Example 18

Rice plants of the variety "Nihonbare" at the 1.5-leaf stage were sprayed until dripping wet with a solution of the compounds according to the invention in a mixture of 40% acetone and 60% water. At the same time, the plants were watered with a solution of the substances in a mixture of 5% acetone and 95% water. 24 hours later, the plants were inoculated by spraying with a pycnospore suspension ($10^6$/ml) of *Pyricularia oryzae*. The plants were stored for 2 days in a darkened controlled-environment cabinet at 26° C. and a relative atmospheric humidity of 99% and then transferred to an illuminated controlled-environment cabinet at about 18° C. and a relative atmospheric humidity of 75–80%. 7–9 days after inoculation the plants were investigated for their infestation with *Pyricularia oryzae*. The following substances were given a rating of 3 or 4 at 500 mg of active substance/l of spray liquor: Compounds according to Example Nos. 47 and 53.

Example 19

Apple seedlings (*Malus sp.*) aged about 3 weeks were sprayed until dripping wet with a solution of the compounds according to the invention in a mixture of 40% acetone and 60% water. After 24 hours the plants were inoculated by spraying with a spore suspension (300,000/ml) of *Venturia inaequalis*. The plants were stored for 2 days in the dark at 18°–20° C. and a relative atmospheric humidity of 99% and then in the light for 5 days at the same atmospheric humidity, and finally for 7 days at 75–80% atmospheric humidity. 14 days after treatment the plants were investigated for their infestation with *Venturia inaequalis*. The following substances were given a rating of 3 or 4 at 500 mg of active substance/l of spray liquor: Compounds according to Example Nos. 46 and 48.

We claim:
1. A compound of the formula I

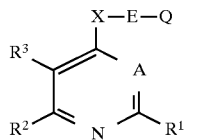

in which
- $R^1$ is hydrogen, halogen, ($C_1$–$C_4$)-alkyl, or ($C_3$–$C_5$)-cycloalkyl; $R^2$ and $R^3$ are identical or different and are each hydrogen, ($C_1$–$C_4$)-alkyl, ($C_1$–$C_4$)-haloalkyl, ($C_2$–$C_4$)alkenyl, ($C_2$–$C_4$)-haloalkenyl, ($C_2$–$C_4$)-alkynyl, ($C_2$–$C_4$)-haloalkynyl, ($C_1$–$C_8$)-trialkylsilylalkynyl, phenyl-($C_1$–$C_8$)-dialkylsilylalkynyl, aryl-($C_1$–$C_2$)-alkyl-($C_1$–$C_8$)-dialkyl-silylalkynyl, ($C_3$–$C_8$)-cycloalkyl-($C_1$–$C_8$)-dialkylsilylalkynyl, (1-methylsila-($C_3$–$C_8$)-cycloalk-1-yl)alkynyl, triphenylsilylalkynyl, ($C_1$–$C_4$)-alkoxy, ($C_1$–$C_4$)-haloalkoxy, ($C_1$–$C_4$)-alkoxy-($C_1$–$C_4$)-alkyl, ($C_1$–$C_4$)-haloalkoxy-($C_1$–$C_4$)-alkyl, ($C_1$–$C_4$)-alkoxy-($C_1$–$C_4$)-haloalkyl, ($C_1$–$C_4$)-haloalkoxy-($C_1$–$C_4$)-haloalkyl, halogen, hydroxyl, ($C_1$–$C_4$)-hydroxyalkyl, ($C_1$–$C_4$)-alkanoyl, ($C_1$–$C_4$)-alkanoyl-($C_1$–$C_4$)-alkyl, ($C_1$–$C_4$)-haloalkanoyl, ($C_3$–$C_5$)-cycloalkyl, ($C_3$–$C_5$)-halocycloalkyl, cyano, ($C_1$–$C_4$)-cyanoalkyl, nitro, ($C_1$–$C_4$)-nitroalkyl, thiocyano, ($C_1$–$C_4$)-thiocyanoalkyl, ($C_1$–$C_4$)-alkoxycarbonyl, ($C_1$–$C_4$)-alkoxycarbonyl-($C_1$–$C_4$)-alkyl, ($C_1$–$C_4$)-haloalkoxycarbonyl, ($C_1$–$C_4$)-alkanoyloxy-($C_1$–$C_4$)-alkyl, ($C_1$–$C_4$)-alkylthio, ($C_1$–$C_4$)-alkylthio-($C_1$–$C_4$)-alkyl, ($C_1$–$C_4$)-haloalkylthio, ($C_1$–$C_4$)-alkylsulfynyl, ($C_1$–$C_4$)-haloalkylsulfynyl, ($C_1$–$C_4$)-alkylsulfonyl or ($C_1$–$C_4$)-haloalkylsulfonyl; where if $R_2$ is hydrogen, ($C_1$–$C_4$)-alkyl, halogen, ($C_1$–$C_4$)-haloalkyl, ($C_1$–$C_4$)-alkoxy, ($C_1$–$C_4$)-haloalkoxy, ($C_1$–$C_4$)-alkoxy-($C_1$–$C_4$)-alkyl, ($C_1$–$C_4$)-alkylthio or ($C_1$–$C_4$)-alkylthio-($C_1$–$C_4$)-alkyl;
- $R^3$ is not simultaneously hydrogen, ($C_1$–$C_4$)-alkyl, ($C_1$–$C_4$)-alkoxy, ($C_1$–$C_4$)-haloalkoxy, halogen or ($C_1$–$C_4$)-alkylthio;
- A is nitrogen;
- X is NH, oxygen or $S(O)_q$ where q is 0, 1 or 2;
- E is a direct bond or a straight-chain or branched ($C_1$–$C_4$)-alkanediyl group;
- Q is defined for $Q^1$, and
- $Q^1$ is a cycloalkyl group of the formula II or II'

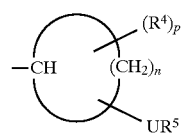

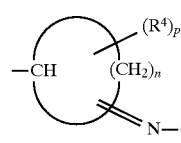

in which n is an integer from 2 to 7;
- $(R^4)_p$ and $UR^5$ are substituents of the isocyclic ring formed with the participation of $(CH_2)_n$;
- p is 1 or 2;
- $R^4$ is hydrogen, halogen, ($C_1$–$C_4$)-alkyl, ($C_1$–$C_4$)-haloalkyl, ($C_1$–$C_4$)alkoxy, or ($C_1$–$C_4$)-alkylthio;
- U is a direct bond, oxygen or a group $S(O)_m$ where m=0, 1 or 2;
- $R^5$ is alkyl, alkenyl, alkynyl, aryl or heterocyclyl, and, if $Q^1$ is a radical of the formula II and U is a direct bond, $R^5$ is also hydroxyl, cyano, thiocyano, nitro or halogen, wherein the aryl or heterocyclyl radicals are optionally substituted up to three—and in the case of fluorine up to the maximum number of—by identical or different substitutents and for one or more nonadjacent saturated carbon units in the alkyl, alkenyl or alkynyl radicals mentioned to be replaced by a carbonyl group or by a heteroatom unit selected from the group consisting of oxygen; $S(O)_x$ where x=0, 1 or 2; $NR^6$; or $SiR^7R^8$, in which $R^6$ is hydrogen, ($C_1$–$C_4$)-alkyl, ($C_1$–$C_4$)alkoxy, or ($C_1$–$C_4$)-alkanoyl and $R^7$ and $R^8$ are ($C_1$–$C_4$)-alkyl; and in which, furthermore, 3 to 12 atoms of these hydrocarbon radicals, which radicals are modified as above if desired, optionally form a ring and these hydrocarbon radicals, with or without the variations indicated, are optionally substituted by one or more identical or different radicals selected from the group consisting of halogen, aryl, aryloxy, arylthio, cycloalkoxy, cycloalkylthio, heterocyclyl, heterocyclyloxy, heterocyclylthio, alkanoyl, cycloalkanoyl, haloalkanoyl, aroyl, arylalkanoyl, cycloalkylalkanoyl, heterocyclylalkanoyl, alkoxycarbonyl, haloalkoxycarbonyl, cycloalkoxycarbonyl, cycloalkylalkoxy-carbonyl, arylalkoxycarbonyl, heterocyclylalkoxycarbonyl, aryloxycarbonyl, heterocyclyloxycarbonyl, alkanoyloxy, haloalkoyloxy, cycloalkanoyloxy, cycloalkylalkanoyloxy, aroyloxy, arylalkanoyloxy, heterocycloylalkanoyloxy, alkylsulfonyloxy, arylsulfonyloxy, hydroxyl, cyano, thiocyano or nitro, wherein said cycloaliphatic, aromatic or heterocyclic ring systems among the substituents just mentioned are optionally substituted by up to three and in the case of fluorine up to the maximum number of identical or different substituents, or Q is as defined for $Q^2$ and $Q^2$ is a radical of the formula III

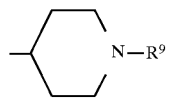

in which $R^9$ is aryl or heteroaromatic ring system and the aryl or heteroaromatic ring system are optionally substituted by up to three—and in the case of fluorine up to the maximum number of—identical or different substituents, or a salt thereof, wherein the substituents for the aromatic and heterocyclic ring systems are halogen, nitro, cyano, di-($C_1$–$C_4$)-alkylamino, ($C_1$–$C_4$)-alkyl, ($C_1$–$C_4$)-trialkylsilyl, ($C_1$–$C_4$)-alkoxy, ($C_1$–$C_4$)-alkoxy-($C_1$–$C_4$)-alkyl, ($C_1$–$C_2$)-alkoxy-$(CH_2CH_2)_{1,2}$-ethoxy, ($C_1$–$C_4$)-alkylthio ($C_1$–$C_4$)-alkylsulfinyl, ($C_1$–$C_4$)-alkylsulfonyl, phenyl, benzyl, phenoxy, phenylthio, halophenoxy, ($C_1$–$C_4$)-alkylphenoxy, ($C_1$–$C_4$)-alkylthiophenoxy, phenylthio, heterocyclyl, heterocyclythio, heterocyclyloxy, haloheterocyclyloxy, alkylheterocyclyloxy or alkoxyheterocyclyloxy, wherein said alkyl radicals and the radicals derived therefrom are optimally substituted one or more times—and in the case of fluorine up to the maximum number of—by halogen and provided that if $R^3$ is halogen, $R^2$ is not ($C_3$–$C_5$)-cycloalkyl
wherein heterocyclyl means a heteroaromatic or heteroaliphatic ring system, where a heteroaromatic ring system is a ($C_6$–$C_{14}$) aryl group in which at least one CH group is replaced by N and/or at least two adjacent CH groups are replaced by S, NH or O and heteroaliphatic ring system is a ($C_3$–$C_8$)-cycloalkyl radical in which at least one carbon unit has been replaced by O, S or a group $N^{11}$, and $R^{11}$ is hydrogen, ($C_1$–$C_4$)-alkyl, ($C_1$–$C_4$)-alkoxy or aryl.

2. A compound of the formula I as claimed in claim 1, in which $R^5$ is ($C_1$–$C_{20}$)-alkyl, ($C_2$–$C_{20}$)alkenyl, ($C_2$–$C_{20}$)-alkynyl, aryl, heterocyclyl, and, if $Q^1$ is a radical of the formula II and U is a direct bond, $R^5$ is also hydroxyl, cyano, thiocyano, nitro or halogen, wherein the aryl or heterocyclyl radicals are optionally substituted up to three—and in the case of fluorine up to the maximum number of—by identical or different substituents and for one or more nonadjacent saturated carbon units in the alkyl, alkenyl or alkynyl radicals mentioned to be replaced by a carbonyl group or by a heteratom unit selected from the group consisting of oxygen; $S(O)_x$ where x=0, 1 or 2; $NR^6$ or $SiR^7R^8$, in which $R^6$ is hydrogen, ($C_1$–$C_4$)-alkyl, ($C_1$–$C_4$)alkoxy, or ($C_1$–$C_4$)-alkanoyl and $R^7$ and $R^8$ are ($C_1$–$C_4$)-alkyl; and in which furthermore 3 to 12 atoms of these hydrocarbon radicals, which radicals are modified as above optionally form a ring and these hydrocarbon radicals, with or without the variations indicated, optionally are substituted by one or more identical or different radicals selected from the group consisting of halogen, aryl, aryloxy, arylthio, ($C_3$–$C_8$)-cycloalkoxy, ($C_3$–$C_8$)-cycloalkylthio, heterocyclyl, heterocyclyloxy, heterocyclylthio, ($C_1$–$C_{12}$)-alkanoyl, ($C_3$–$C_8$)cycloalkanoyl, ($C_1$–$C_{12}$)haloalkanoyl, aryl-($C_1$–$C_4$)-alkanoyl, ($C_3$–$C_8$)-cycloalkyl-($C_1$–$C_4$)-alkanoyl, heterocyclyl-($C_1$–$C_4$)-alkanoyl, ($C_1$–$C_{12}$)-alkoxycarbonyl, ($C_1$–$C_{12}$)-haloalkoxycarbonyl, ($C_3$–$C_8$)-cycloalkoxycarbonyl, ($C_3$–$C_8$)-cycloalkyl-($C_1$–$C_4$)-alkoxycarbonyl, aryl-($C_1$–$C_4$)-alkoxycarbonyl, heterocyclyl-($C_1$–$C_4$)-alkoxycarbonyl, aryloxycarbonyl, heterocyclyloxycarbonyl, ($C_1$–$C_{12}$)-alkanoyloxy, ($C_2$–$C_{12}$)-haloalkanoylalkoxy, ($C_3$–$C_8$)-cycloalkanoyloxy ($C_3$–$C_8$)-cycloalkyl-($C_1$–$C_4$)-alkanoyloxy, aroyloxy, aryl-($C_1$–$C_4$)-alkanoyloxy, heterocyclyl-($C_1$–$C_4$)-alkanoyloxy, ($C_1$–$C_{12}$)-alkylsulfonyloxy, arylsulfonyloxy, hydroxyl, cyano, thiocyano, or nitro, wherein said cycloaliphatic, aromatic or heterocyclic ring systems among the substituents just mentioned are optionally substituted by up to three—and in the case of fluorine up to the maximum number of—by identical or different substituents, or a salt thereof.

3. A compound of formula I as claimed in claim 1, wherein Q is as defined for $Q^1$, n is 5 and E is a direct bond, and the groups -X-E and $UR^5$ are in the cis configuration relative to one another and take up positions 1 and 4 on the cyclohexane ring, or a salt thereof.

4. A compound of the formula I as claimed in claim 1, in which $R^1$ is hydrogen or fluorine;

$R^2$ and $R^3$ are ($C_1$–$C_4$)-alkyl, ($C_2$–$C_4$)-alkenyl, ($C_2$–$C_4$)-alkynyl, trimethylsilylethynyl, methoxycarbonyl, ($C_1$–$C_4$)-haloalkyl, halogen, methoxymethyl or cyano;

A is N;

X is NH or oxygen;

U is oxygen or a direct bond;

E is a direct bond;

n is 5; the radicals X and $UR^5$ or $NOR^5$ take up positions 1 and 4 on the cyclohexane ring and X and $UR^5$ are in the cis configuration relative to one another;

$R^4$ is hydrogen, ($C_1$–$C_4$)-alkyl, trifluoromethyl or ($C_1$–$C_4$)-alkoxy, or a salt thereof.

5. A compound of the formula I as claimed in claim 1, in which $R^1$ is hydrogen;

$R^2$ is methyl, ethyl, vinyl, ethynyl, trimethylsilylethynyl, ($C_1$–$C_2$)-fluoroalkyl or methoxymethyl;

$R^3$ is vinyl, ethynyl, trimethylsilylethynyl, methyl, ethyl, ($C_1$–$C_2$)-fluroralkyl, cyano or halogen;

A is nitrogen;

X is NH;

E is a direct bond;

$R^4$ is hydrogen;

n is 5;

Q is a radical of the formula II in which the substituents X and $UR^5$ take up positions 1 and 4 on the cyclohexane ring and are in each case in the cis configuration relative to one another, or Q is a radical of the formula II' in which the substituent X and the oxime ether group take up positions 1 and 4 on the cyclohexane ring;

$R^5$ is ($C_1$–$C_{12}$)-alkyl, ($C_2$–$C_{12}$)-alkenyl, ($C_2$–$C_{12}$)alkynyl, aryl or heterocyclyl wherein the aryl or heterocyclyl radicals are unsubstituted or to be substituted by up to three—and in the case of fluorine up to the maximum number of—by identical or different substituents and for one, two or three, carbon unit in the alkyl radicals mentioned to be replaced by heteroatom unit selected from the group consisting of oxygen; sulfur or $SiR^7R^8$, where $R^7$ and $R^8$ are ($C_1$–$C_4$)alkyl, and in which, furthermore, 3 to 12 atoms of theses hydrocarbon radicals, which radicals can if desired be modified as above, optionally form a ring and these hydrocarbon radicals, with or without the variations indicated, are optionally substituted by one or more,—and in the case of halogen up to the maximum number of—by identical or different radicals selected from the group consisting of aryl, arylthio, heterocyclyl, heterocyclyloxy, heterocyclylthio and alkoxycarbonyl, wherein said aromatic or heterocyclic ring systems among the substituents just mentioned are optimally substituted by up to three—and in the case of fluorine up to the maximum number of—by identical or different substituents, or a salt thereof.

6. A process for the preparation of a compound of the formula I as claimed in claim 1, which comprises reacting a compound of the formula IV

(IV)

in which A, $R^1$, $R^2$ and $R^3$ are as defined under formula I and L is a leaving group selected from the group consisting of halogen, alkylthio, alkanesulfonyloxy, arylsulfonyloxy, alkylsulfonyl or arylsulfonyl, with a nucleophile of the formula V

H—X-E-Q (V)

in which X, E and Q are as defined above for formula I.

7. A process for the preparation of a compound of the formula VI

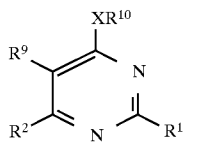

(VI)

in which
- $R^1$ is hydrogen, halogen, ($C_1$–$C_4$)-alkyl, or ($C_3$–$C_5$)-cycloalkyl;
- $R^2$ is hydrogen, ($C_1$–$C_4$)-alkyl, ($C_1$–$C_4$)-haloalkyl, ($C_2$–$C_4$)alkenyl, ($C_2$–$C_4$)-haloalkenyl, ($C_2$–$C_4$)-alkynyl, ($C_2$–$C_4$)-haloalkynyl, ($C_1$–$C_8$)-trialkylsilylalkyryl, phenyl-($C_1$–$C_8$)-dialkylsilylalkynyl, aryl-($C_1$–$C_2$)-alkyl-($C_1$–$C_8$)-dialkyl-silylalkynyl, ($C_3$–$C_8$)-cycloalkyl-($C_1$–$C_8$)-dialkylsilylalkynyl, (1-methylsila-($C_3$–$C_8$)-cycloalk-1-yl)alkynyl, triphenylsilylalkynyl, ($C_1$–$C_4$)-alkoxy, ($C_1$–$C_4$)-haloalkoxy, ($C_1$–$C_4$)-alkoxy-($C_1$–$C_4$)-alkyl, ($C_1$–$C_4$)-haloalkoxy-($C_1$–$C_4$)-alkyl, ($C_1$–$C_4$)-alkoxy-($C_1$–$C_4$)-haloalkyl, ($C_1$–$C_4$)-haloalkoxy-($C_1$–$C_4$)-haloalkyl, halogen, hydroxyl, ($C_1$–$C_4$)-hydroxyalkyl, ($C_1$–$C_4$)-alkanoyl, ($C_1$–$C_4$)-alkanoyl-($C_1$–$C_4$)-alkyl, ($C_1$–$C_4$)-haloalkanoyl, ($C_3$–$C_5$)-cycloalkyl, ($C_3$–$C_5$)-halocycloalkyl, cyano, ($C_1$–$C_4$)-cyanoalkyl, nitro, ($C_1$–$C_4$)-nitroalkyl, thiocyano, ($C_1$–$C_4$)-thiocyanoalkyl, ($C_1$–$C_4$)-alkoxycarbonyl, ($C_1$–$C_4$)-alkoxycarbonyl-($C_1$–$C_4$)-alkyl, ($C_1$–$C_4$)-haloalkoxycarbonyl, ($C_1$–$C_4$)-alkanoyloxy-($C_1$–$C_4$)-alkyl, ($C_1$–$C_4$)-alkylthio, ($C_1$–$C_4$)-alkylthio-($C_1$–$C_4$)-alkyl, ($C_1$–$C_4$)-haloalkylthio, ($C_1$–$C_4$)-alkylsulfynyl, ($C_1$–$C_4$)-haloalkylsulfynyl, ($C_1$–$C_4$)-alkylsulfonyl or ($C_1$–$C_4$)-haloalkylsulfonyl;
- X is NH, oxygen or $S(O)_q$ where q is 0, 1, or 2;
- $R^5$ is ($C_1$–$C_4$)-perfluoroalkyl, trifluoromethylthio, cyano or ($C_1$–$C_4$)-alkoxy, and when $R^9$ is ($C_1$–$C_4$)-alkoxy, $R^2$ is also ($C_1$–$C_4$)-alkyl;
- $R^{10}$ is the unit E-Q, wherein
  - E is a direct bond or a straight-chain or branched ($C_1$–$C_4$)-alkanediyl group;
  - Q is defined for $Q^1$, and
- $Q^1$ is a cycloalkyl group of the formula II or II'

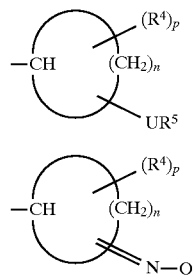

in which n is an integer from 2 to 7;
- $(R^1)_p$ and $UR^5$ are substituents of the isocyclic ring formed with the participation of $(CH_2)_n$;
- p is 1 or 2;
- $R^4$ is hydrogen, halogen, ($C_1$–$C_4$)-alkyl, ($C_1$–$C_4$)-haloalkyl, ($C_1$–$C_4$)alkoxy, or ($C_1$–$C_4$)-alkylthio;
- U is a direct bond, oxygen or a group $S(O)_m$ where m=0, 1 or 2;
- $R^5$ is alkyl, alkenyl, alkynyl, aryl or heterocyclyl, and, if $Q^1$ is a radical of the formula II and U is a direct bond, $R^5$ is also hydroxyl, cyano, thiocyano, nitro or halogen, wherein the aryl or heterocyclyl radicals are optionally substituted up to three—and in the case of fluorine up to the maximum number of—by identical or different substitutents and for one or more nonadjacent saturated carbon units in the alkyl, alkenyl or alkynyl radicals mentioned to be replaced by a carbonyl group or by a heteroatom unit selected from the group consisting of oxygen; $S(O)_x$ where x=0, 1 or 2; $NR^6$; or $SiR^7R^8$, in which $R^6$ is hydrogen, ($C_1$–$C_4$)-alkyl, ($C_1$–$C_4$)alkoxy, or ($C_1$–$C_4$)-alkanoyl and $R^7$ and $R^8$ are ($C_1$–$C_4$)-alkyl; and in which, furthermore, 3 to 12 atoms of these hydrocarbon radicals, which radicals are modified as above if desired, optionally form a ring and these hydrocarbon radicals, with or without the variations indicated, are optionally substituted by one or more identical or different radicals selected from the group consisting of halogen, aryl, aryloxy, arylthio, cycloalkoxy, cycloalkylthio, heterocyclyl, heterocyclyloxy, heterocyclylthio, alkanoyl, cycloalkanoyl, haloalkanoyl, aroyl, arylalkanoyl, cycloalkylalkanoyl, heterocyclylalkanoyl, alkoxycarbonyl, haloalkoxycarbonyl, cycloalkoxycarbonyl, cycloalkylalkoxy-carbonyl, arylalkoxycarbonyl, heterocyclylalkoxycarbonyl, aryloxycarbonyl, heterocyclyloxycarbonyl, alkanoyloxy, haloalkoyloxy, cycloalkanoyloxy, cycloalkylalkanoyloxy, aroyloxy, arylalkanoyloxy, heterocycloylalkanoyloxy, alkylsulfonyloxy, arylsulfonyloxy, hydroxyl, cyano, thiocyano or nitro, wherein said cycloaliphatic, aromatic or heterocyclic ring systems among the substituents just mentioned are optionally substituted by up to three and in the case of fluorine up to the maximum number of identical or different substituents, or Q is as defined for $Q^2$ and $Q^2$ is a radical of the formula III

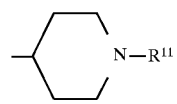

(III)

in which $R^{11}$ is aryl or heteroaromatic ring system and the aryl or heteroaromatic ring system are optionally substituted by up to three—and in the case of fluorine up to the maximum number of—identical or different substituents, or a salt thereof, wherein the substituents for the aromatic and heterocyclic ring systems are halogen, nitro, cyano, di-($C_1$–$C_4$)-alkylamino, ($C_1$–$C_4$)-alkyl, ($C_1$–$C_4$)-trialkylsilyl, ($C_1$–$C_4$)-alkoxy, ($C_1$–$C_2$)-alkoxy-($C_1$–$C_4$)-alkyl, ($C_1$–$C_2$)-alkoxy-($CH_2CH_2$)$_{1,2}$-ethoxy, ($C_1$–$C_4$)-alkylthio ($C_1$–$C_4$)-alkylsulfinyl, ($C_1$–$C_4$)-alkylsulfonyl, phenyl, benzyl, phenoxy, halophenoxy, ($C_1$–$C_4$)-alkylphenoxy, ($C_1$–$C_4$)-alkylthiophenoxy, phenylthio, heterocyclyl, heterocyclythio, heterocyclyloxy, haloheterocyclyloxy, alkylheterocyclyloxy or alkoxyheterocyclyloxy, wherein said alkyl radicals and the radicals derived therefrom are optimally substituted one or more times—and in the case of fluorine up to the maximum number of—by halogen;
- $R^{10}$ is a ($C_1$–$C_{20}$)-alkyl radical in which one or more, nonadjacent saturated carbon units are optionally replaced by heteroatom units selected from the group consisting of oxygen; $S(O)_x$ where x=0, 1 or 2; $NR^{6'}$ or $SiR^{7'}R^{8'}$, where $R^{6'}$ is hydrogen, ($C_1$–$C_4$)-alkyl, ($C_1$–$C_4$)-alkanoyl or ($C_1$–$C_4$)-alkoxy, and where $R^{7'}$ and $R^{8'}$ are ($C_1$–$C_4$)-alkyl, and in which furthermore these alkyl radicals, with or without the variations indicated, are optionally substituted by one or more times—and in the case of halogen up to the maximum number of—identical or different radicals selected from the group consisting of halogen, aryl, aryloxy, arylthio, cycloalkoxy, cycloalkylthio, heterocyclyl, heterocyclyloxy, heterocyclylthio, alkanoyl, cycloalkanoyl, haloalkanoyl, aroyl, arylalkanoyl, cycloalkylalkanoyl, heterocyclylalkanoyl, alkoxycarbonyl, haloalkoxycarbonyl, cycloalkoxycarbonyl, cycloalkylalkoxycarbonyl, arylalkoxycarbonyl, heterocyclylalkoxycarbonyl, aryloxycarbonyl, heterocyclyloxycarbonyl, alkanoyloxy, haloalkanoyloxy, cycloalkanoyloxy, cycloalkylalkanoyloxy, aroyloxy, arylalkanoyloxy, heterocycloylalkanoyloxy, alkylsulfonyloxy, arylsulfonyloxy, hydroxyl, cyano, thiocyano or nitro, wherein the cycloaliphatic, aromatic or heterocyclic ring systems among the substituents just mentioned to be unsubstituted or substituted by up to three—and in the case of fluorine up to the maximum number of—identical or different substituents, wherein the substituent for the aliphatic, aromatic or heterocyclic ring systems are halogen, nitro, cyano, di-$(C_1-C_4)$-alkylamino, $(C_1-C_4)$-alkyl, $(C_1-C_4)$-trialkylsilyl, $(C_1-C_4)$-alkoxy, $(C_1-C_4)$-alkoxy-$(C_1-C_4)$-alkyl, $(C_1-C_2)$-alkoxy-$[CH_2CH_2]_{1,2}$-ethoxy, $(C_1-C_4)$-alkylthio, $(C_1-C_4)$-alkylsulfinyl, $(C_1-C_4)$-alkylsulfonyl, phenyl, benzyl, phenoxy, phenylthio, halophenoxy, $(C_1-C_4)$-alkylphenoxy, $(C_1-C_4)$-alkoxyphenoxy, $(C_1-C_4)$-alkylthiophenoxy, heterocyclyl, heterocyclylthio, heterocyclyloxy, haloheterocyclyloxy, alkylheterocyclyloxy or alkoxyheterocyclyloxy, where in the alkyl radicals and the radicals derived therefrom one or more—and in the case of fluorine up to the maximum number of—hydrogen atoms can be replaced by halogen; and wherein heterocyclyl means a heteroaromatic or heteroaliphatic ring system, where a heteroaromatic ring system is a $(C_6-C_{14})$ aryl group in which at least one CH group is replaced by N and/or at least two adjacent CH groups are replaced by S, NH or O and heteroaliphatic ring system is a $(C_3-C_8)$-cycloalkyl radical in which at least one carbon unit has been replaced by O, S or a group $N^{12}$, and $R^{12}$ is hydrogen, $(C_1-C_4)$-alkyl, $(C_1-C_4)$-alkoxy or aryl which comprises reacting a compound of the formula VII

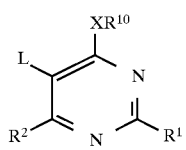

(VII)

for which $R^1$, $R^2$, A, X and $R^{10}$ are as defined for formula VI and, if $R^9$ is $(C_1-C_4)$-alkoxy, $R^2$ is also $(C_1-C_4)$-alkyl, and L is a leaving group selected from the group consisting of halogen, alkylthio, alkanesulfonyloxy, arylsulfonyloxy, alkylsulfonyl or arylsulfonyl with a compound $MR^9$, where M is an alkali metal or alkaline earth metal.

8. A compound of the formula VI in which $R^1$, $R^2$, and $R^9$, and X are as defined in claim 6 for formula VI and $R^{10}$ is a $(C_1-C_{20})$-alkyl radical in which one or more, nonadjacent saturated carbon units are optionally replaced by heteroatom units, selected from the group consisting of oxygen; $S(O)_x$; where X=0, 1 or 2; $NR^{6'}$ or $SiR^{7'}R^{8'}$, where $R^{6'}$ is hydrogen, $(C_1-C_4)$-alkyl, $(C_1-C_4)$-alkanoyl or $(C_1-C_4)$-alkoxy, and where $R^{7'}$ and $R^{8'}$ are $(C_1-C_4)$-alkyl, and in which furthermore these alkyl radicals with or without the variations indicated, are optionally substituted by one or more, identical or different radicals selected from the group consisting of halogen, aryl, aryloxy, arylthio, cycloalkoxy, cycloalkylthio, heterocyclyl, heterocyclyloxy, heterocyclylthio, alkanoyl, cycloalkanoyl, haloalkanoyl, aroyl, arylalkanoyl, cycloalkylalkanoyl, heterocyclylalkanoyl, alkoxycarbonyl, haloalkoxycarbonyl, cycloalkoxycarbonyl, cycloalkylalkoxycarbonyl, arylalkoxycarbonyl, heterocyclylalkoxycarbonyl, aryloxycarbonyl, heterocyclyloxycarbonyl, alkanoyloxy, haloalkanoyloxy, cycloalkanoyloxy, cycloalkylalkanoyloxy, aroyloxy, arylalkanoyloxy, heterocycloylalkanoyloxy, alkylsulfonyloxy, arylsulfonyloxy, hydroxyl, cyano, thiocyano or nitro, wherein the cycloaliphatic, aromatic or heterocyclic ring systems among the substituents just mentioned to be unsubstituted or substituted by up to three—and in the case of fluorine up to the maximum number of—identical or different substitutents.

9. A fungicidal composition comprising a fungicidally effective quantity of at least one compound as claimed in claim 1 together with the additives or auxiliaries which are customary for this application.

10. An insecticidal, acaricidal, ixodicidal or nematicidal composition, comprising an effective quantity of at least one compound as claimed in claim 1 together with the additives or auxiliaries which are customary for this application.

11. A plant protection composition comprising a fungicidally, insecticidally, acaricidally or nematicidally effective quantity of at least one compound as claimed in claim 1 and at least one further active substance, from the series consisting of fungicides, insecticides, attractants, sterilants, acaricides, nematicides and herbicides, together with the auxiliaries and additives which are customary for this application.

12. A composition for use in protecting wood or as a preservative in sealing compounds, in paints, in cooling lubricants for metalworking or in drilling and cutting oils, which comprises an effective quantity of at least one compound as claimed in claim 1 together with the auxiliaries and additives which are customary for these applications.

13. A composition for controlling endo- or ectoparasites, which comprises an effective quantity for this application of a compound as claimed in claim 1 and a physiologically acceptable carrier.

14. A method of controlling phytopathogenic fungi, which comprises applying a fungicidally effective quantity of a compound as claimed in claim 1 to these fungi or to the plants, areas or substrates infested with them or to seed.

15. A method of controlling insect pests, acarids, molluscs and nematodes, which comprises applying an effective quantity of a compound as claimed in claim 1 to these insect pests, acarids, molluscs and nematodes or to the plants, areas or substrates infested with them.

16. A method of controlling endo- or ectoparasites, which comprises the administration of an effective quantity for this application of a compound as claimed in claim 1.

17. Seed, treated or coated with an effective quantity of a compound as claimed in claim 1.

18. Seed, treated or coated with an effective quantity of a composition as claimed in claim 9.

19. A compound according to claim 1, wherein the aryl radical has 6 to 12 carbon atoms and the heterocyclyl radical is selected from the group consisting of thiophene, furan, pyrrole, thiazole, oxazole, imidazole, isothiazole, isoxazole, pyrazole, 1,3,4-oxadiazole, 1,3,4-thiadiazole, 1,3,4-triazole, 1,2,4-oxadiazole, 1,2,4-thiadiazole, 1,2,4-triazole, 1,2,3-triazole, 1,2,3,4-tetrazole, benzo[b]thiophene, benzo[b]furan, indole, benzo[c]thiophene, benzo[c]furan, isoindole, benzoxazole, benzothiazole, benzimidazole, benzisoxazole, benzisothiazole, benzopyrazole, benzothiadiazole, benzotriazole, dibenzofuran, dibenzothiophene, carbazole, pyridine, pyridine, pyrazine, pyrimidine, pyridazine, 1,3,5-triazine, 1,2,4-triazine, quinoline, isoquinoline, quinoxaline, quinazoline, cinnoline, 1,8-naphthyridine, 1,5-naphthyridine, 1,6-naphthyridine, 1,7-naphthyridine, phthalazine, pyridopyrimidine, purine, pteridine or 4H-quinolizine.

* * * * *

UNITED STATES PATENT AND TRADEMARK OFFICE
CERTIFICATE OF CORRECTION

PATENT NO. : 5,852,023
DATED : December 22, 1998
INVENTOR(S) : Schaper, et al.

It is certified that error appears in the above-identified patent and that said Letters Patent is hereby corrected as shown below:

On the title page: Item

In [75] Inventors: of the Patent, change "Schaper, Schaper" to --Schaper, Diedorf--.

Under the FOREIGN PATENT DOCUMENTS section of the Patent, change "A 44 17 163" to --DE-A 44 17 163--.

In column 14, line 44 of the Patent, add --Scheme 2--.

In column 15, line 1 of the Patent, above the words Scheme 2, add --continued--.

In column 16, line 35 of the Patent, replace the current structure (Ik) with

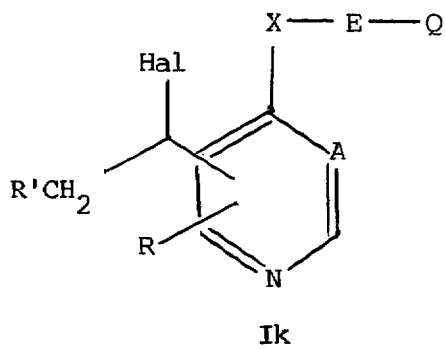

In column 29, line 33 of the Patent, change "5-Cyanoethyl-6" to --5-Cyano-6-ethyl-4--.

UNITED STATES PATENT AND TRADEMARK OFFICE
CERTIFICATE OF CORRECTION

PATENT NO. : 5,852,023
DATED : December 22, 1998
INVENTOR(S) : Schaper, et al.

It is certified that error appears in the above-identified patent and that said Letters Patent is hereby corrected as shown below:

<u>IN THE CLAIMS:</u>

In Claim 1, column 43, line 35 of the Patent, change "$R_2$" to -- $R^2$ --.

In Claim 7, column 47, line 14 of the Patent, change "trialkylsilylalkyryl" to -- trialkylsilylalkynyl --.

In Claim 7, column 47, line 35 of the Patent, change "$R^5$" to -- $R^9$ --.

In Claim 7, column 47, line 56 of the Patent, change "$(R^1)_p$" to -- $(R^4)_p$ --.

In Claim 7, column 48, line 59 of the Patent, between "is" and "a" add -- furthermore --.

In Claim 8, column 49, line 60 of the Patent, change "formilla" to --formula--.

In Claim 8, column 49, line 61 of the Patent, change "claim 6" to --claim 7--.

Signed and Sealed this

Twelfth Day of October, 1999

Attest:

Attesting Officer

Q. TODD DICKINSON

Acting Commissioner of Patents and Trademarks